(12) United States Patent
Sater et al.

(10) Patent No.: US 6,893,446 B2
(45) Date of Patent: May 17, 2005

(54) MANUAL BONE ANCHOR PLACEMENT DEVICES

(75) Inventors: Ghaleb A. Sater, Lynnfield, MA (US); Armand Morin, Berkley, MA (US); Barry N. Gellman, North Easton, MA (US); Steven P. Beaudet, Littleton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 175 days.

(21) Appl. No.: 10/442,446

(22) Filed: May 21, 2003

(65) Prior Publication Data

US 2003/0204191 A1 Oct. 30, 2003

Related U.S. Application Data

(62) Division of application No. 09/817,403, filed on Mar. 26, 2001, now Pat. No. 6,589,249, which is a division of application No. 09/309,816, filed on May 11, 1999, now Pat. No. 6,241,736.
(60) Provisional application No. 60/125,207, filed on Mar. 18, 1999, and provisional application No. 60/085,113, filed on May 12, 1998.

(51) Int. Cl.$^7$ ............................................. A61B 17/58
(52) U.S. Cl. ....................................................... 606/104
(58) Field of Search ........................ 606/104, 86, 139, 606/142, 144, 99; 81/52, 58.3

(56) References Cited

U.S. PATENT DOCUMENTS

| | | |
|---|---|---|
| 1,030,530 A | 6/1912 | Palmer |
| 1,179,910 A | 4/1916 | Greenfield |
| 1,417,669 A | 5/1922 | Langworthy |
| 2,200,120 A | 5/1940 | Nauth |
| 2,655,921 A | 10/1953 | Haboush |

(Continued)

FOREIGN PATENT DOCUMENTS

| | | |
|---|---|---|
| EP | 0 241 240 | 10/1987 |
| EP | 0 558 993 | 9/1993 |
| EP | 0 599 772 | 6/1994 |
| EP | 0 686 373 | 6/1995 |
| FR | 95 11543 | 9/1995 |

(Continued)

OTHER PUBLICATIONS

Product Literature on ANCHORLOK™, Wright Medical Technology, Inc. 1995.
Product Literature on Influence In–Fast Bone Screw System, Apr. 24, 1998 from webstie: www.influencemedical.com/products/products.html.

(Continued)

*Primary Examiner*—Eduardo C. Robert
(74) *Attorney, Agent, or Firm*—Ropes & Gray LLP

(57) ABSTRACT

Manual bone anchor placement devices include a lever, a force translator and a rotary force mechanism. The devices are substantially gun- or pistol-shaped and are actuated when a user squeezes the lever to the gripping portion of a handle. Manual, linear force on the lever is mechanically translated through the force translator to the rotary force mechanism which transmits a rotary force to a securing element, or coupler, which mates with a bone anchor screw. The rotation of the securing element or coupler applies a torque on the bone anchor screw thereby placing the screw into bone. Kits comprising any of: a molded flexible sleeve for enclosing a suture, a retaining clip for preventing the suture from slipping out of the sleeve, a buttress-shaped bone anchor screw comprising a micropolished eyelet for receiving a suture, and a suture which may, or may not be pre-attached to the bone anchor screw, are disclosed. A collapsible, protective cover for a bone anchor screw is also disclosed.

6 Claims, 33 Drawing Sheets

U.S. PATENT DOCUMENTS

| | | |
|---|---|---|
| 2,707,783 A | 5/1955 | Sullivan |
| 2,830,479 A | 4/1958 | Finn |
| 3,388,847 A | 6/1968 | Kasulin |
| 3,892,232 A | 7/1975 | Neufeld |
| 3,593,903 A | 5/1976 | Lawrence et al. |
| 3,953,896 A | 5/1976 | Treace |
| 3,971,271 A | 7/1976 | Wagner et al. |
| 4,159,716 A | 7/1979 | Borchers |
| 4,204,623 A | 5/1980 | Green |
| 4,422,567 A | 12/1983 | Haynes |
| 4,483,562 A | 11/1984 | Schoolman |
| 4,527,726 A | 7/1985 | Assell et al. |
| 4,537,185 A | 8/1985 | Stednitz |
| 4,576,167 A | 3/1986 | Noiles |
| 4,606,343 A | 8/1986 | Conta et al. |
| 4,632,100 A | 12/1986 | Somers et al. |
| 4,632,101 A | 12/1986 | Freedland |
| 4,635,634 A | 1/1987 | Santos |
| 4,664,305 A | 5/1987 | Blake, III et al. |
| 4,738,255 A | 4/1988 | Goblea et al. |
| 4,739,751 A | 4/1988 | Sapega et al. |
| 4,784,137 A | 11/1988 | Kulik et al. |
| 4,856,385 A | 8/1989 | Ogilvie et al. |
| 4,870,957 A | 10/1989 | Goble et al. |
| 4,940,467 A | 7/1990 | Tronzo |
| 5,002,550 A | 3/1991 | Li |
| 5,019,078 A | 5/1991 | Perren et al. |
| 5,037,422 A | 8/1991 | Hayhurst |
| 5,037,426 A | 8/1991 | Goble et al. |
| 5,040,715 A | 8/1991 | Green et al. |
| 5,052,607 A | 10/1991 | Dutton |
| 5,057,112 A | 10/1991 | Sherman et al. |
| 5,061,181 A | 10/1991 | Niznick |
| 5,064,434 A | 11/1991 | Haber |
| 5,067,956 A | 11/1991 | Buford, III et al. |
| 5,084,050 A | 1/1992 | Draenert |
| 5,100,417 A | 3/1992 | Cerier et al. |
| 5,102,421 A | 4/1992 | Anspach, Jr. |
| 5,116,338 A | 5/1992 | Poggie et al. |
| 5,141,520 A | 8/1992 | Goble et al. |
| 5,149,329 A | 9/1992 | Richardson |
| 5,180,382 A | 1/1993 | Frigg et al. |
| 5,190,543 A | 3/1993 | Schlapfer |
| 5,203,784 A | 4/1993 | Ross et al. |
| 5,217,462 A | 6/1993 | Asnis et al. |
| 5,224,946 A | 7/1993 | Hayhurst et al. |
| 5,236,359 A | 8/1993 | Myers |
| 5,258,016 A | 11/1993 | DiPoto et al. |
| 5,268,001 A | 12/1993 | Nicholson et al. |
| 5,289,963 A | 3/1994 | McGarry et al. |
| 5,328,077 A | 7/1994 | Lou |
| 5,370,662 A | 12/1994 | Stone et al. |
| 5,381,943 A | 1/1995 | Allen et al. |
| 5,411,506 A | 5/1995 | Goble et al. |
| 5,443,482 A | 8/1995 | Stone et al. |
| D362,909 S | 10/1995 | Warner |
| 5,458,603 A | 10/1995 | Futch |
| 5,464,407 A | 11/1995 | McGuire |
| 5,470,334 A | 11/1995 | Ross et al. |
| 5,520,696 A | 5/1996 | Wenstrom, Jr. |
| 5,520,700 A | 5/1996 | Beyar |
| 5,522,843 A | 6/1996 | Zang |
| 5,544,664 A | 8/1996 | Benderev et al. |
| 5,573,548 A | 11/1996 | Nazre et al. |
| 5,591,207 A | 1/1997 | Coleman |
| 5,607,432 A | 3/1997 | Fucci |
| 5,611,515 A | 3/1997 | Benderev et al. |
| 5,674,247 A | 10/1997 | Sohn |
| 5,683,418 A | 11/1997 | Luscombe et al. |
| 5,690,677 A | 11/1997 | Schmieding et al. |
| 5,697,931 A | 12/1997 | Thompson |
| 5,702,397 A | 12/1997 | Goble et al. |
| 5,720,766 A | 2/1998 | Zang et al. |
| 5,725,529 A | 3/1998 | Nicholson et al. |
| 5,735,849 A | 4/1998 | Baden et al. |
| 5,755,726 A | 5/1998 | Pratt et al. |
| 5,782,862 A | 7/1998 | Bonutti |
| 5,824,011 A | 10/1998 | Stone et al. |
| 5,842,478 A | 12/1998 | Benderev et al. |
| 5,851,219 A | 12/1998 | Goble et al. |
| 6,039,686 A | 3/2000 | Kovac |
| 6,139,565 A | 10/2000 | Stone et al. |
| 6,406,480 B1 | 6/2002 | Beyar |

FOREIGN PATENT DOCUMENTS

| | | |
|---|---|---|
| FR | 2 718 012 | 10/1995 |
| GB | 1044633 | 10/1966 |
| GB | 2268690 | 1/1994 |
| WO | 89/10096 | 11/1989 |
| WO | 92/16152 | 10/1992 |
| WO | 94 04080 | 3/1994 |
| WO | 95/15726 | 6/1995 |
| WO | 95/16399 | 6/1995 |
| WO | 96/06567 | 3/1996 |
| WO | WO 96/25887 | 8/1996 |
| WO | 96/28100 | 9/1996 |
| WO | WO 97/06731 | 2/1997 |
| WO | 97/13465 | 4/1997 |
| WO | 97/30638 | 8/1997 |
| WO | WO 97/30638 | 8/1997 |
| WO | WO 97/41792 | 11/1997 |
| WO | 98/12971 | 4/1998 |

OTHER PUBLICATIONS

Benderev, "A modified percutaneous outpatient bladder neck suspension system." J. Urology 152: 2316–2320 (1994).

Hurson et al., "The use of spiked plastic washers in the repair of avulsed ligaments." Acta Orthop. Scand. 52:23–26 (1981).

Mascio, Therapy of urinary stress incontinence in women: using Mitek® GII Anchors, Mitek® Brochure, 1993.

O'Carroll et al., "A technique of medical ligament repair of the knee with cancellous screws and spiked washers." Injury 15: 99–104 (1983).

Parra et al., "Experience with a simplified technique for the treatment of female stress urinary incontinence." British J. Urology 66: 615–617 (1990).

Pederson et al., "Mitek® Anchor System: A new technique for Tenodesis and Ligamentous repair of the foot and ankle." J. Foot Surgery 30: 48–51 (1991).

Richmond et al., "Modification of the Bankart reconstruction with a suture anchor: Report of a new technique." Am. J. Sports Med. 19: 343–346 (1991).

Wolf et al., "Arthroscopic Bankart repair using suture anchors, operative techniques in orthopaedics." 1(2): 187–191 (1991).

International Search Report for PCT/US99/10275.

Influence Inc.: Products: Incontinence (http://www.influencemedical.com/products) May 23, 2000.

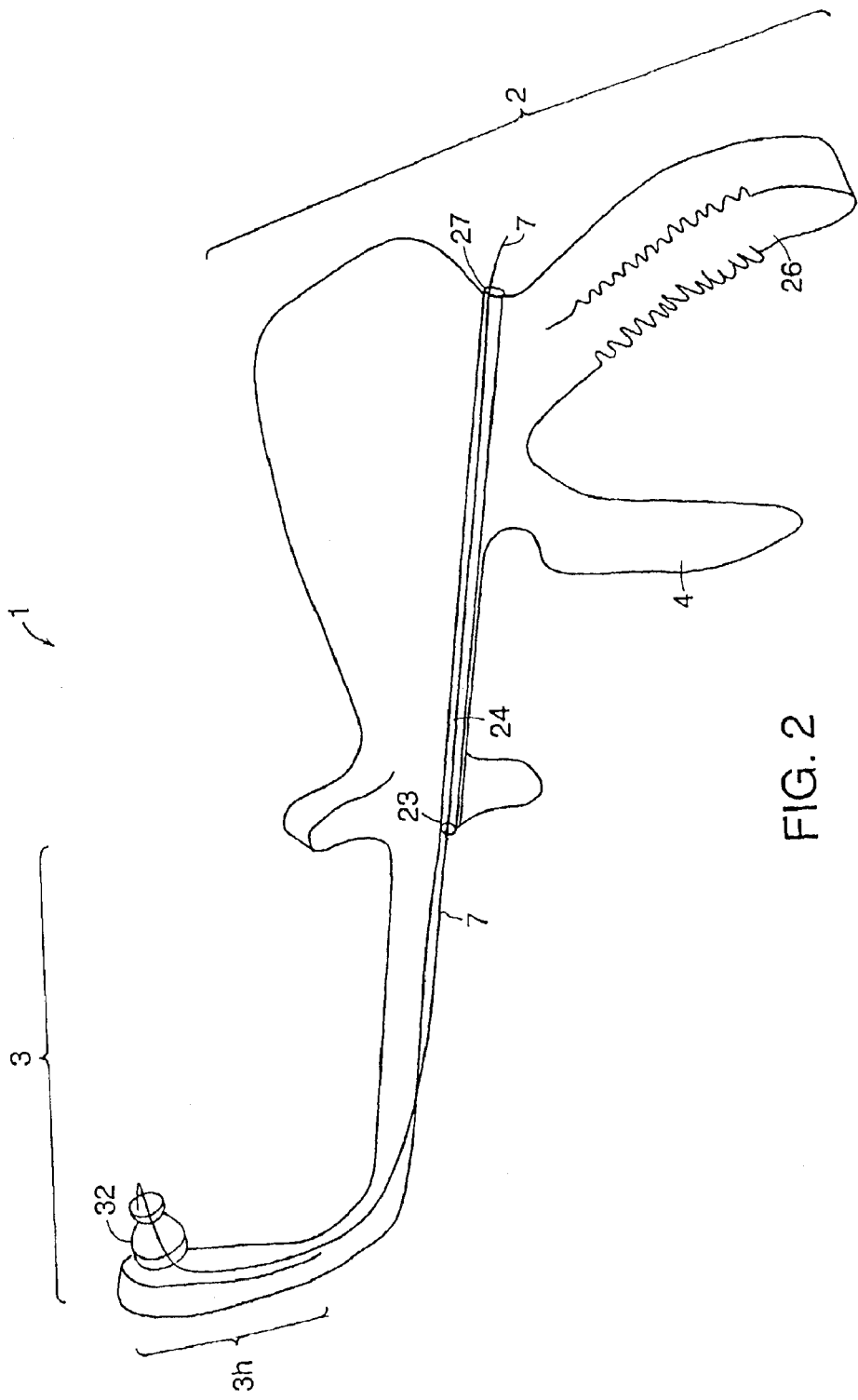

MANUAL BONE ANCHOR PLACEMENT DEVICES

CROSS-REFERENCE TO RELATED APPLICATIONS

This application is a divisional of U.S. application Ser. No. 09/817,403, filed Mar. 26, 2001, now U.S. Pat. No. 6,589,249, which is a divisional of U.S. application Ser. No. 09/309,816, filed May 11, 1999; now U.S. Pat. No. 6,241,736, which relates to, and claims the benefit of and priority to, provisional U.S. Patent Application Ser. Nos. 60/085,113, filed May 12, 1998, and 60/125,207; filed on Mar. 18, 1999. The entirety of these provisional applications is hereby incorporated herein by reference.

TECHNICAL FIELD

This invention relates to devices for manually placing or implanting bone anchor screws into bone and to methods of using these devices.

BACKGROUND INFORMATION

In elderly women, the bladder and proximal urethra tend to descend from their normal anatomic positions such that the bladder neck and proximal urethra move away from the posterior wall of the pubic bone, producing a condition known as stress urinary incontinence (SUI). This condition may be treated surgically, using sutures to fasten periurethral tissue to the pubic bone as a means of repositioning and resuspending the bladder and proximal urethra. The sutures are anchored to the pubic bone using bone anchor screws.

Bone anchor placement devices, such as bone anchor drivers, may be used to place a bone anchor screw at a selected insertion site in the bone. Either percutaneous or transvaginal surgical procedures may be performed using such devices. Percutaneous procedures require an incision in the abdominal wall and/or anterior vaginal wall in order to introduce the bone anchor placement device and are necessarily invasive and traumatic to the patient. Transvaginal such procedures are cost-limiting and may not be readily available when required to perform surgery. Typical bone anchor placement devices used in transvaginal procedures are configured like power drills and are cannulated.

A suture may be threaded into a bone anchor screw prior to, or after, its insertion into the pubic bone. Load on a suture at the point of attachment of the suture to the bone anchor screw can cause breakage of the suture requiring additional, undesired surgery.

SUMMARY OF THE INVENTION

The present invention relates to manual bone anchor placement devices. The manual bone anchor placement devices disclosed herein are particularly useful in transvaginal methods of treating female urinary incontinence, although they can be used in other medical applications. The devices of the present invention are designed to permit rotational insertion of a bone anchor screw and to provide low cost alternatives to powered cannulated drills. The devices may be disposable or may be modular in nature, thereby allowing interchange of parts for reuse.

An advantage of the disclosed manual bone anchor placement devices is that they eliminate the need for a percutaneous incision to access an insertion area, although the devices can be used in a percutaneous procedure. A transvaginal approach to inserting a bone anchor screw into the pubic bone is far less invasive than a percutaneous procedure, thus a transvaginal procedure is far less traumatic for the patient.

An additional advantage of the disclosed manual bone anchor placement devices is that they seat a self-tapping bone anchor screw with a pre-attached suture. Since the bone anchor screw used with the disclosed devices is self-tapping and the suture is pre-attached, it is unnecessary for the physician to prebore a hole into the bone, remove the drill, introduce a seating device, seat the bone anchor screw, and then thread the suture. Single-step insertion of the bone anchor screw and suture not only reduces the total time required for the procedure, it also greatly reduces the possibility that the physician may lose access to the bored hole or seated bone anchor screw. Thus, the possible need to drill additional holes and/or seat additional bone anchor screws is reduced.

The manual bone anchor placement devices disclosed herein provide a mechanism to translate linear force exerted by a user on a lever into rotary force on a bone anchor screw. In one aspect of the invention, the manual bone anchor placement device comprises a manually-actuatable lever, a resilient element, a force translator, and a rotator. The force translator is coupled at its distal end to the lever and at its proximal end to the resilient element. The resilient element is coupled to the rotator. Linear force on the lever is transmitted through the force translator to the resilient element and from the resilient element to the rotator. The rotator rotates in response to this force. The device may further comprise a securing element coupled to the rotator which mates with a bone anchor screw and rotates when the rotator rotates, thereby applying a torque on the bone anchor screw, placing the bone anchor screw into bone.

In another aspect of the invention, the manual bone anchor placement device comprises a manually-actuatable lever, a force translator, a rack, and a rotator. The force translator comprises a distal end and a proximal end, the distal end receiving force from the lever, the proximal end being coupled to the rack. The force translator transmits force to the rack which moves linearly into an engaging position in response to this force. The rotator is positioned in close proximity to the rack for engagement with the rack when the rack moves into the engaging position. Engagement of the rotator by the rack causes the rotator to rotate. The device may further comprise a coupler coupled to the rotator which mates with a bone anchor screw and rotates when the rotator rotates, placing the bone anchor screw into bone.

In another aspect of the invention, a manual bone anchor placement device is disclosed which comprises a manually-actuatable lever, a driver rod comprising threads, and a cup and washer positioned over the threads. The cup is coupled to the lever and moves axially along the driver rod upon actuation of the lever, engaging with the washer. When the cup and washer engage each other, linear force transmitted from the lever through the cup is translated to a rotary force on the driver rod, rotating the driver rod. The device may further comprise a coupling element for mating with a bone anchor screw, and for rotating when the driver rod rotates to place the bone anchor screw into bone.

The present invention also relates to a self-tapping buttress-shaped bone anchor screw. The bone anchor screw of the present invention comprises a micropolished eyelet for receiving a suture. The eyelet may be circular, ellipsoidal, or tear-drop shaped. The bone anchor screw described herein is designed to require less torque to seat and to minimize load on a pre-attached suture in comparison with known bone anchor screws.

Kits are also disclosed comprising any of: a molded flexible sleeve for enclosing a suture, a retaining clip for preventing the suture from slipping out of the sleeve, a buttress-shaped bone anchor screw comprising a micropolished eyelet for receiving a suture, and a suture which may, or may not, be pre-attached to the bone anchor screw. A collapsible, protective cover for a bone anchor screw is also disclosed.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention.

FIG. 2 shows a perspective side view of a manual bone anchor placement device according to one embodiment of the present invention. In this embodiment, the manual bone anchor placement device comprises a groove cut into the outer surface of the handle through which a suture is threaded and the shaft of the manual bone anchor placement is angled upwards at a 90 degree angle.

FIG. 4A shows a cross-sectional view of an embodiment where the rotator comprises a floating pawl. FIG. 4B shows an enlarged cross-sectional view of a rotator which comprises three floating pawls. FIG. 4C shows a three-dimensional cut-away view of the head end of the shaft in an embodiment of the invention where the rotator comprises two floating pawls. FIG. 4D shows a three-dimensional cut-away view of the head end of the shaft in an embodiment of the invention where the rotator comprises a single floating pawl.

FIGS. 5A–D show enlarged views of a securing element which comprises a Hex-shaped recess in its mating portion for mating with a bone anchor screw with a Hex-shaped shaft at its base. FIG. 5A is a perspective view of the securing element showing the Hex-shaped recess. FIG. 5B is a cross-sectional view through the engaging portion of the securing element. FIG. 5C is a perspective side-view of the securing element. FIG. 5D is a view from the top of the securing element. FIG. 5E shows a bone anchor screw which comprises a Hex-shaped shaft at its base. FIG. 5F shows a perspective view of a securing element whose mating portion comprises a Hex-shaped protrusion. FIG. 5G shows a perspective side view of a securing element whose mating portion comprises a Hex-shaped protrusion. FIG. 5H shows an enlarged view of a bone anchor screw with a Hex-shaped recess at its base for mating with a securing element whose mating portion comprises a Hex-shaped protrusion.

FIG. 6A shows a perspective view. FIG. 6B shows a side view. FIG. 6C shows a cross-sectional view.

FIG. 7A shows a perspective view. FIG. 7B shows a side view. FIG. 7C shows a cross-sectional view.

FIG. 8A shows a perspective view where the flat spring portion is slightly bent. FIG. 8B shows a side view of a flat spring portion which is slightly bent. FIG. 8C shows a perspective view where the flat spring portion is lying flat.

FIG. 18A shows an action mechanism which transmits a pull force on a force translator. FIG. 18B shows an action mechanism which transmits a push force on a force translator.

FIG. 23A shows a cross-sectional view of a driver rod comprising grooves to interface with protrusions on a washer. FIG. 23B shows a cross-sectional view of a washer with corresponding protrusions to interface with the grooves in the driver rod. FIG. 23C shows a perspective side view of a cup and washer assembly on a driver rod in which the washer is in a "free-floating" or non-engaged position. FIG. 23D shows a perspective side-view of a cup and washer assembly in which the washer is in an engaged position.

FIG. 24A shows a cross-sectional view from one side of a cup and washer assembly positioned on a driver rod which includes a cover plate. FIG. 24B shows a cross-sectional view from the top of the cup and washer assembly.

DESCRIPTION

Figure 1A:
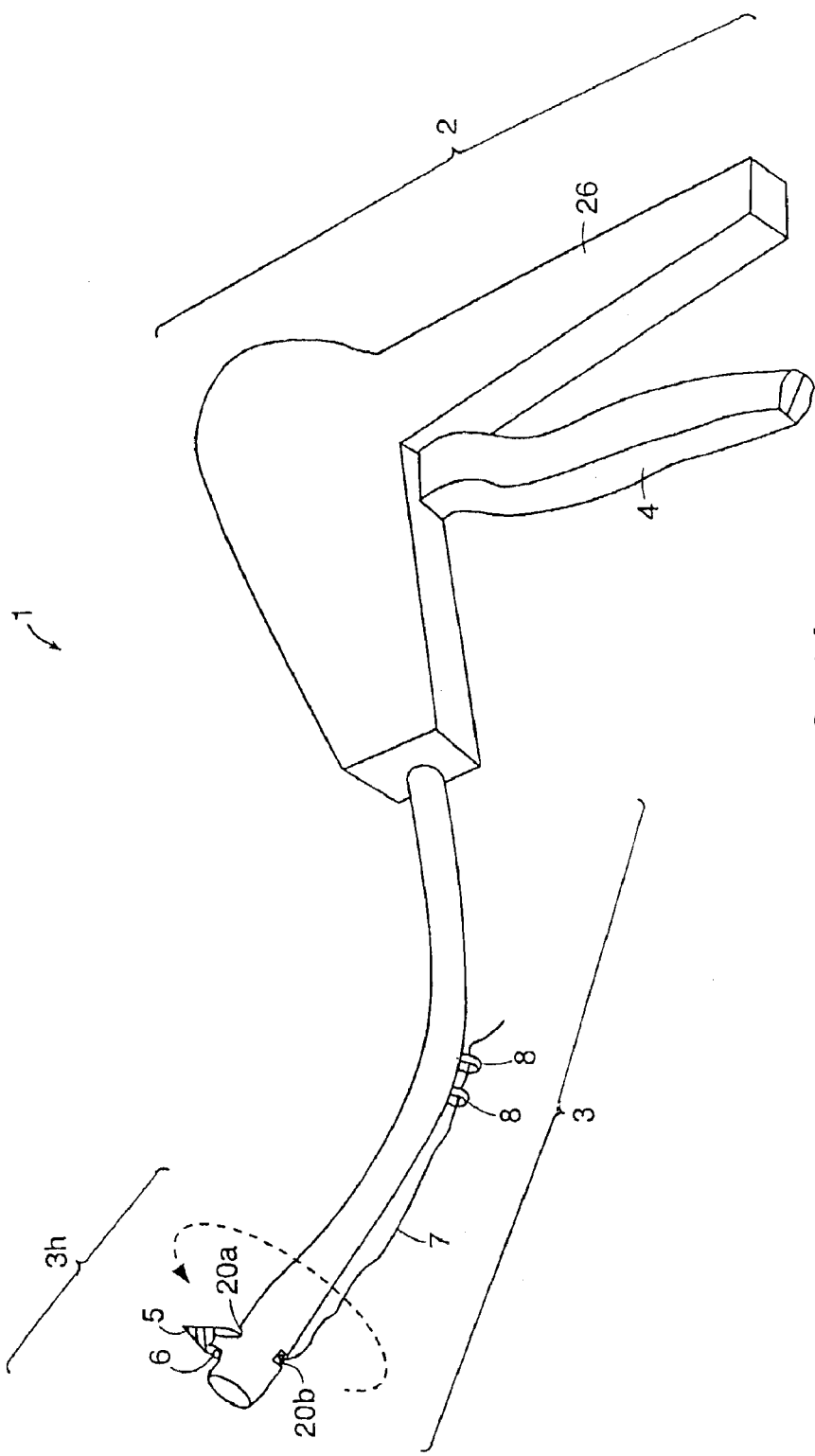
FIG. 1A is a perspective side view of a manual bone anchor placement device within the scope of the present invention.

The manual bone anchor placement devices disclosed provide a mechanism to translate manually linear force (i.e., an operator's hand squeezing a lever) into rotary force on a bone anchor screw. As used herein "placing a bone anchor screw" (or grammatical equivalents thereof) refers to rotational action on, and/or screwing in, of a bone anchor screw into bone. Manual actuation of the disclosed devices occurs when the operator squeezes or pulls a lever with, for example, a single hand. Force on the lever is mechanically transmitted through a force translator to a rotary force mechanism. Each of the disclosed devices are distinguishable by the type of rotary force mechanism used.

In one embodiment of the invention, a manual bone anchor placement device uses a rotary force mechanism which comprises a resilient element wrapped around a rotator ("wrap-around manual bone anchor placement device"). In a second embodiment of the invention, a manual bone anchor placement device ("rack and rotator manual bone anchor placement device") uses a rotary force mechanism which comprises a rack and rotator assembly. In a third embodiment of the invention, a manual bone anchor placement device uses a rotary force mechanism which comprises a cup and washer assembly ("cup and washer manual bone anchor placement device"). A self-tapping bone anchor screw with a pre-attached suture is also disclosed which may be used with any of the aforementioned manual bone anchor placement devices. All of the devices are useful in, for example, transvaginal bone anchor screw insertion procedures.

Wrap-Around Manual Bone Anchor Placement Device

In the embodiment of the invention shown in FIG. 1, the manual bone anchor placement device 1 is substantially pistol- or gun-shaped. In this embodiment, the manual bone placement device 1 comprises a handle 2 and a shaft 3. The handle 2 comprises a gripping portion 26 to facilitate gripping by the user and a lever 4 through which the user may manually transmit force to the bone anchor placement device 1.

Figure 3A:
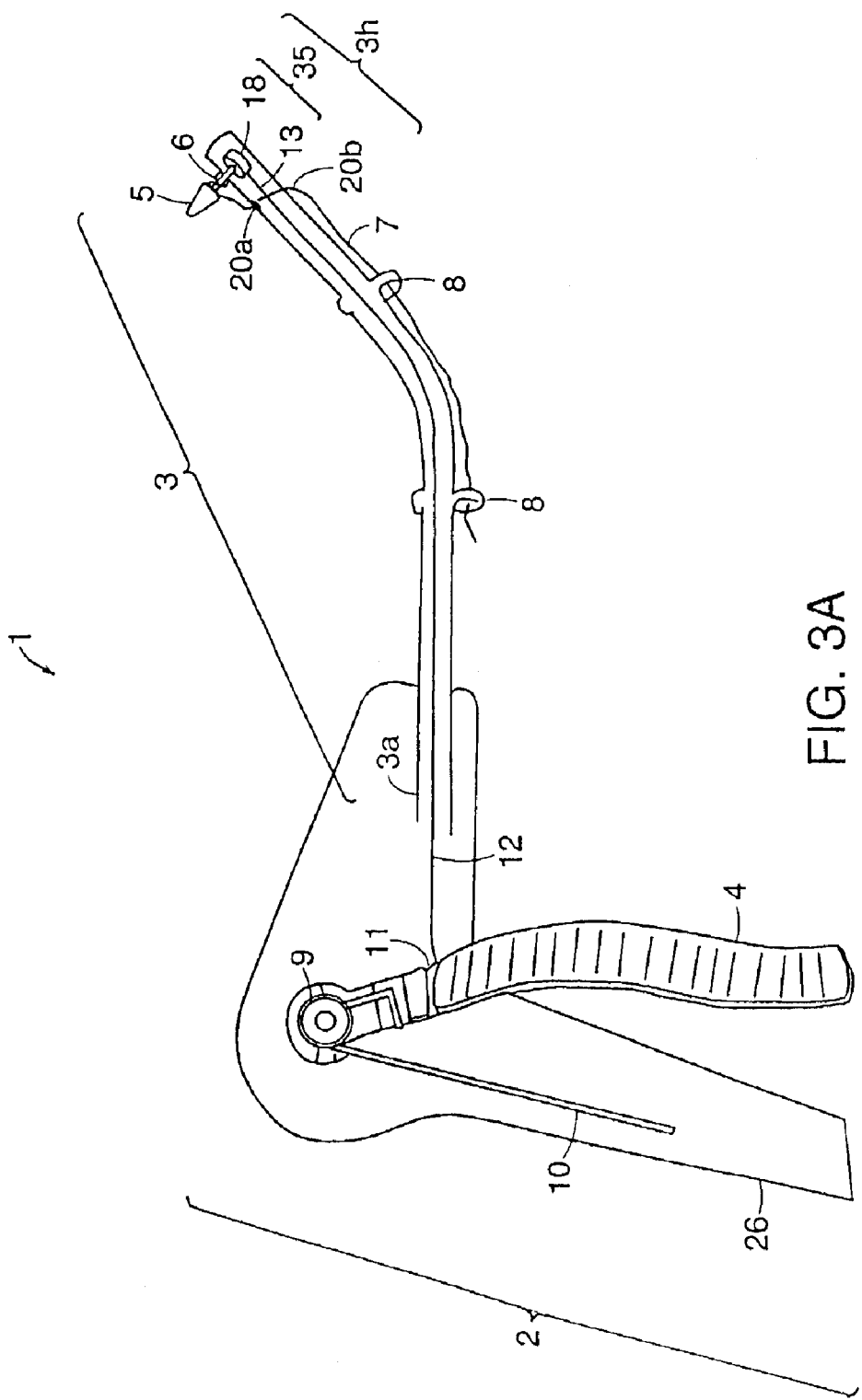
FIG. 3A is a side view of a cross-section through a wrap-around manual bone anchor screw placement device according to one embodiment of the invention showing the components of an action mechanism and a wrap-around rotary force mechanism in which a resilient element is wrapped around a rotator.

As shown in FIG. 3A, the shaft 3 comprises a first end 3a, proximal to the handle 2, and a second end or head end 3h, distal to the handle 2. A force translator 12 runs through the shaft 2 and transmits linear force exerted manually on the lever 4 to a head assembly 35 positioned at the second end 3h of the shaft 3 (shown enlarged in FIG. 4A). The head assembly 35 is capable of engaging with a bone anchor screw 5 and comprises the mechanism which translates linear force from the force translator 12 to rotary force on the bone anchor screw 5.

The shaft 3 is curved to facilitate correct placement of the bone anchor placement device 1 to the proper bone anchor screw 5 insertion site. The shaft 3 is generally linear at its proximal or first end 3a and angles upward near its head end 3h. The upward angle can be from 0 to about 135 degrees. In one embodiment of the invention, the upward angle is between about 75 and about 100 degrees. In another embodiment of the, invention, shown in FIG. 2, the upward angle is approximately 90 degrees. In some embodiments of the invention, the shaft 3 can be rotated 360 degrees relative to the handle 2 (see dashed arrow in FIG. 1A).

As shown in FIG. 3A, the handle 2 of the manual bone anchor placement device 1 of the present invention may further comprise an action mechanism through which force from the lever 4 is transmitted to the force translator 12. The action mechanism comprises the lever 4, a pivot 9, and the proximal end of the force translator 12. The force translator 12 is connected to the lever 4 by a connector 11 which is positioned beneath the pivot 9. The action mechanism further comprises a torsional spring 10 which abuts the lever 4 in the handle 2.

Figure 3B:
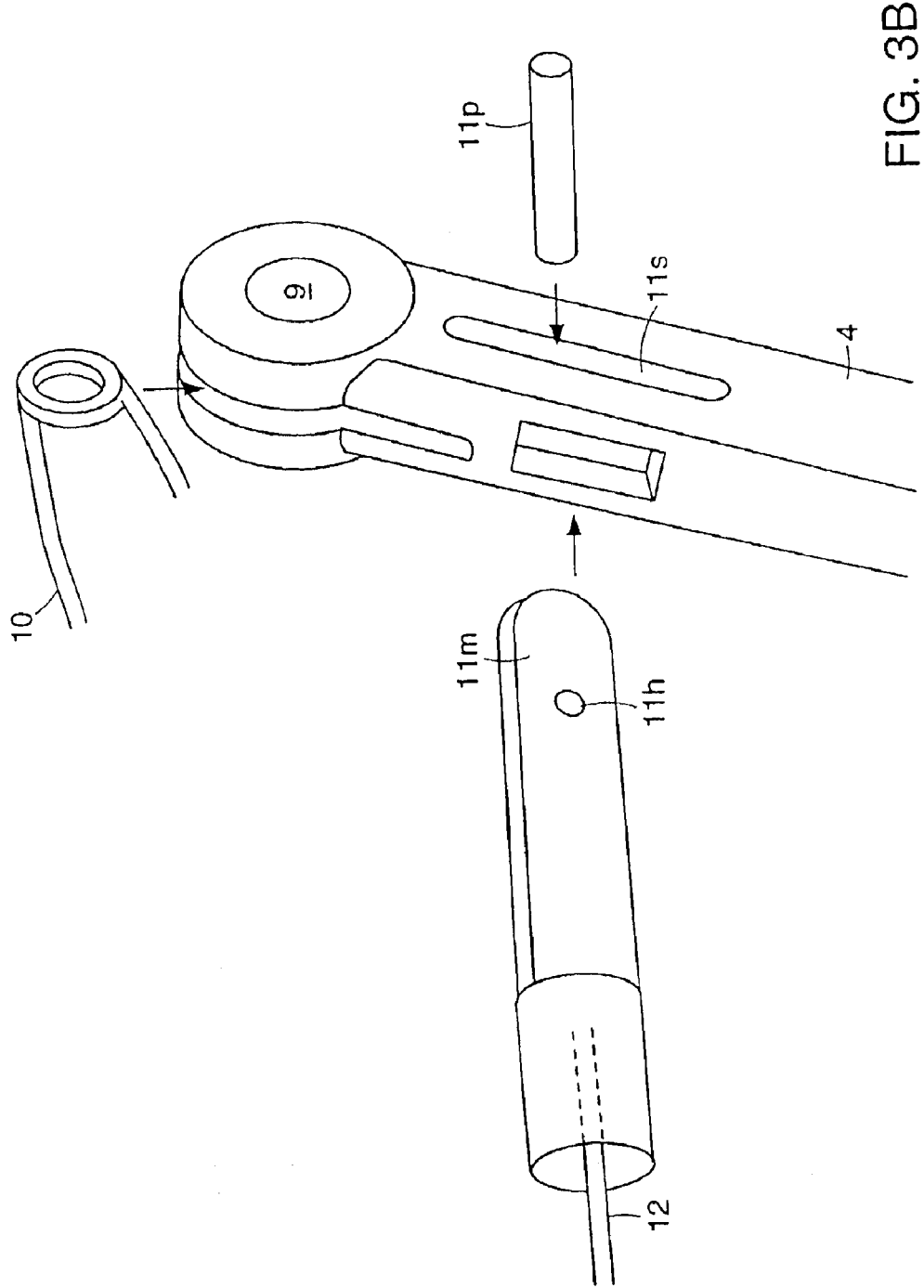
FIG. 3B is an enlarged perspective view of a connector and lever arrangement in an action mechanism according to one embodiment of the invention.

In one embodiment of the invention shown in FIG. 3B, the connector 11 comprises a "slot and pin arrangement." In this embodiment, a slot 11s is included in the portion of the lever 4 proximal to the pivot 9 and defines openings in the sides, front, and back, of the lever 4. A connector member 11m is configured to fit in the slot 11s and further comprises a pinhole 11h. The connector member 11m is coupled to the force translator 12 at the end of the connector member 11m distal to the pinhole 11h. The connector member is positioned within the slot 11s and secured by a pin 11p which extends through both the slot 11s and the pinhole 11h.

In the embodiment of the invention shown in FIG. 3A, the lever 4 extends at least partially from the handle 2 and linear force on the lever 4 is exerted by pulling on the lever 4. Because the pivot 9 is located above the connector 11, the translator 12 is subjected to tensile loading (e.g., a pulling force) during activation and compressive loading (e.g., a pushing force) during release. The torsional spring 10 abutting the lever 4 thus forces the lever 4 into its original position for the next stroke.

Force exerted on the lever 4 is translated as linear force through the force translator 12. As shown in FIG. 3A, the force translator 12 is a substantially linear member which extends from the handle 2 through the shaft 3 of the manual bone anchor device 1. The force translator 12 may be rigid or flexible, so long as it is tensile. In one embodiment of the invention, the force translator 12 is a wire. Additional types of force translators 12 include, but are not limited to, a cable, a rod, suture material, a string, and the like. Suitable force translator 12 materials include metal, plastic, polymers (e.g., nylon, in the case of suture materials), copolymers, and the like.

Figure 4B:
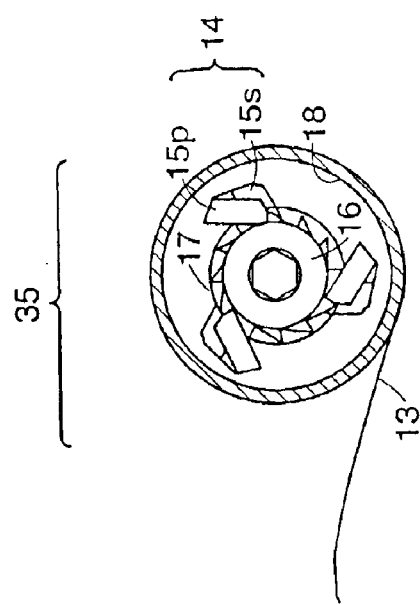
FIGS. 4A–D show views of the head end of a wrap-around manual bone anchor placement device in different embodiments of the invention.
Figure 4A:
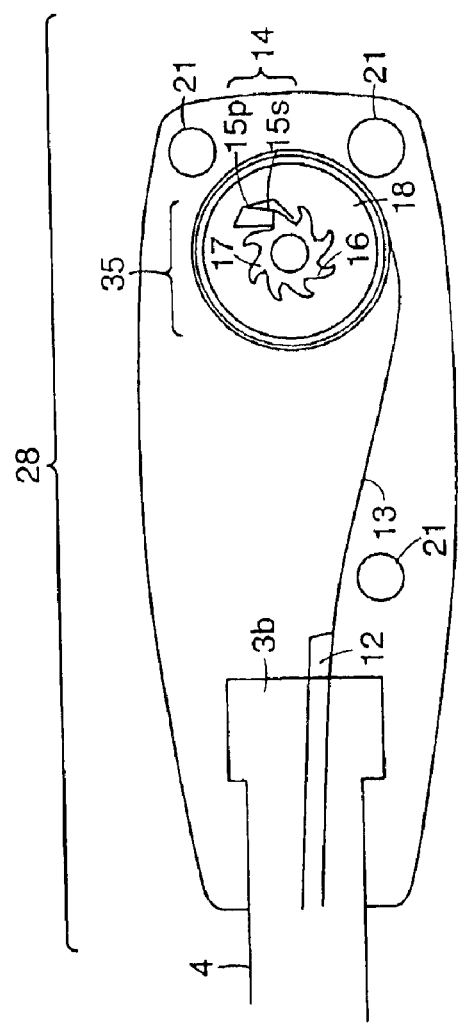

In a further embodiment of the invention, washers 21 are positioned on the inside of the shaft 3 to reduce the friction caused by the force translator 12 contacting the inside surfaces of the shaft 3 (see FIG. 4A). The washers 21 can be made of Teflon® material or any material with a low coefficient of friction.

The section of the shaft portion 3 which seats the head assembly 35 may be simply a wider extension of the head end 3h of the shaft 3 as in FIG. 3A. Alternatively, the head assembly 35 may be provided within a head module 28 seated on the distal-most tip 3b of the shaft (as in FIGS. 4A, 4C, and 4D, for example) and may be either integral with the shaft 3 or separable from the shaft 3. The head assembly 35 comprises a rotator 14, a securing element 166, and a resilient element 13, shown in more detail in FIGS. 4A–D. The resilient element 13 is coupled to both force translator 12 and the rotator 14. In one embodiment of the invention, as shown in FIGS. 4C and 4D, the resilient element 13 is a constant force spring which is welded to the end of the force translator 12 which is proximal to the rotator 14.

Force is transmitted through the resilient element 13 to the rotator 14 which rotates in response to this force. The rotator 14 comprises at least one protruding portion 15p, shown in more detail in FIGS. 4C and 4D and is capable of frictionally and mechanically engaging with the securing element 166 (shown in more detail in FIGS. 5A, 5C, 5F, and 5G). The securing element 166 further comprises an enaging portion 16 and a mating portion 6. The mating portion 6 of the securing element 166 extends at least partly from the head end 3h of the shaft 3, or the head module 28, and mates with a bone anchor screw 5.

Figure 4C:
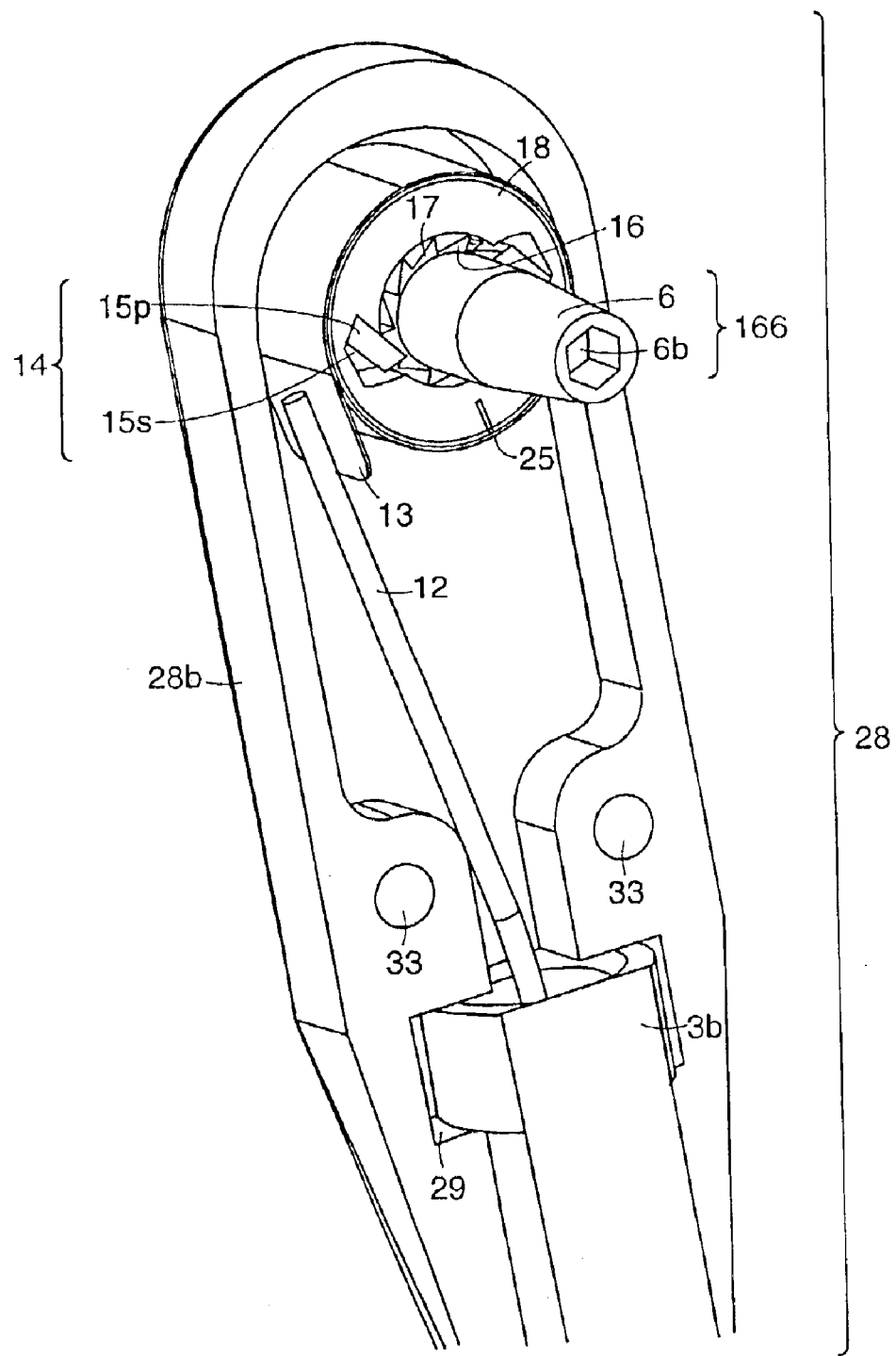
Figure 4D:
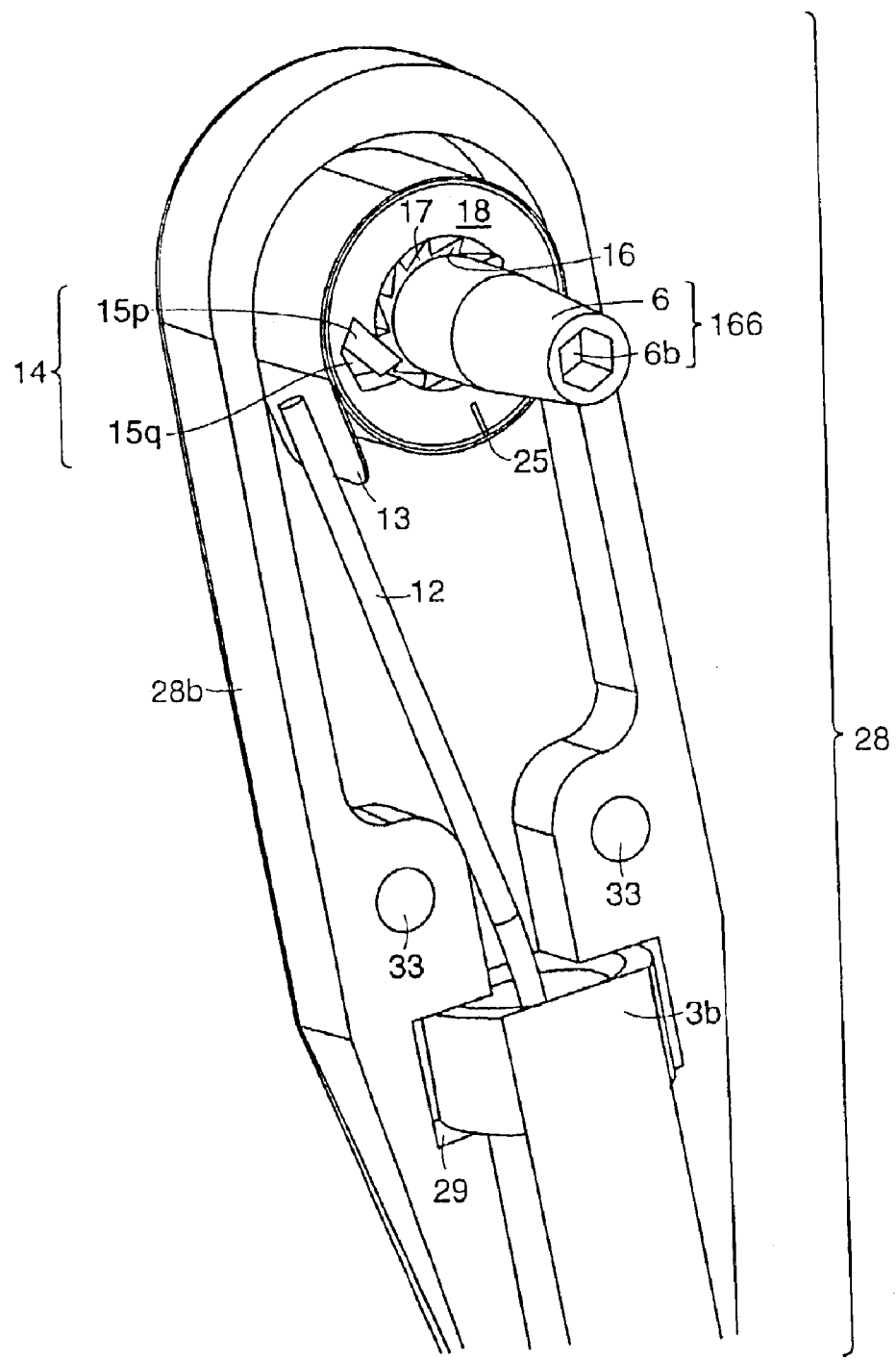
Figure 8A:
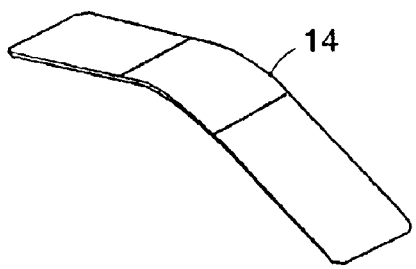
FIGS. 8A–C show enlarged views of the flat spring portion of a floating pawl used in a wrap-around manual bone anchor placement device.
Figure 8B:
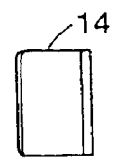
Figure 8C:
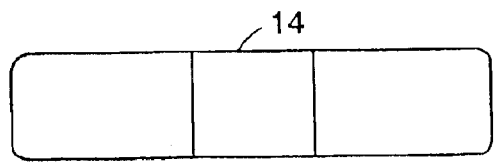

In the embodiment of the invention shown in FIGS. 4A–C, the rotator 14 comprises at least one floating pawl and the engaging portion 16 of securing element 166 has teeth 17 which are capable of meshing with the protruding portion 15p of the floating pawl and rotating in response to the rotation of the pawl. The protruding portion 15p extends from a flat spring member 15s as shown in FIGS. 4C and 4D. The flat spring member 15s may be angled or bent, as shown in more detail in FIGS. 8A–C, to control the position of the protruding portion 15p of, the pawl.

It will be readily apparent to one of ordinary skill in the art that any number and type of protruding portions 15p may be provided so long as they are able to frictionally and mechanically engage with the engaging portion 16 of the securing element 166 to cause rotation of the securing element 166. In the embodiment of the invention shown in FIG. 4B, the rotator 14 comprises three floating pawls which are spaced equidistant from each other about a central axis of rotation. In another embodiment of the invention, shown in FIG. 4C, the rotator 14 comprises two floating pawls, and the teeth 17 of the engaging portion 16 are designed to allow one-directional engagement with the pawls. Slip-free rotation of a bone anchor screw 5 is provided by this design.

Figure 6A:
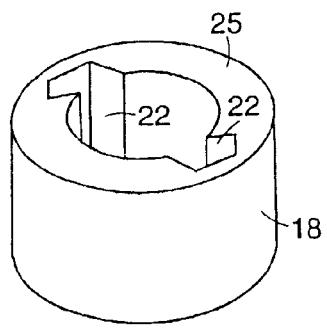
FIGS. 6A–C show enlarged views of the rotatable housing used in a wrap-around manual bone anchor placement device.
Figure 6B:
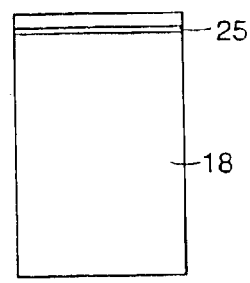
Figure 6C:
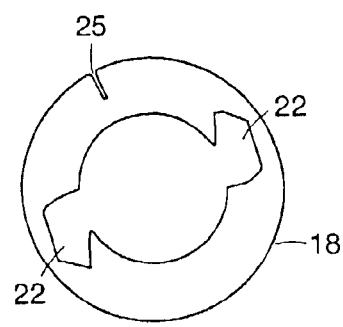
Figure 7A:
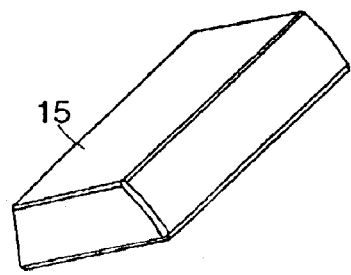
FIGS. 7A–C show enlarged views of the floating portion of a floating pawl used in a wrap-around manual bone anchor placement device.
Figure 7B:
Figure 7C:
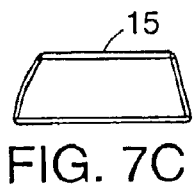

In the embodiment of the invention shown in FIGS. 4C and 4D, the rotator 14 is contained within a rotatable housing 18 positioned within the head module 28 and is fitted into at least one groove 22 within the inner wall of the rotatable housing 18. FIGS. 6A–C show enlarged views of the rotatable housing 18. In the embodiment of the invention shown in FIGS. 6A and 6C, the rotatable housing 18 comprises two grooves 22 to accommodate a rotator 14 that comprises two floating pawls.

Figure 9:
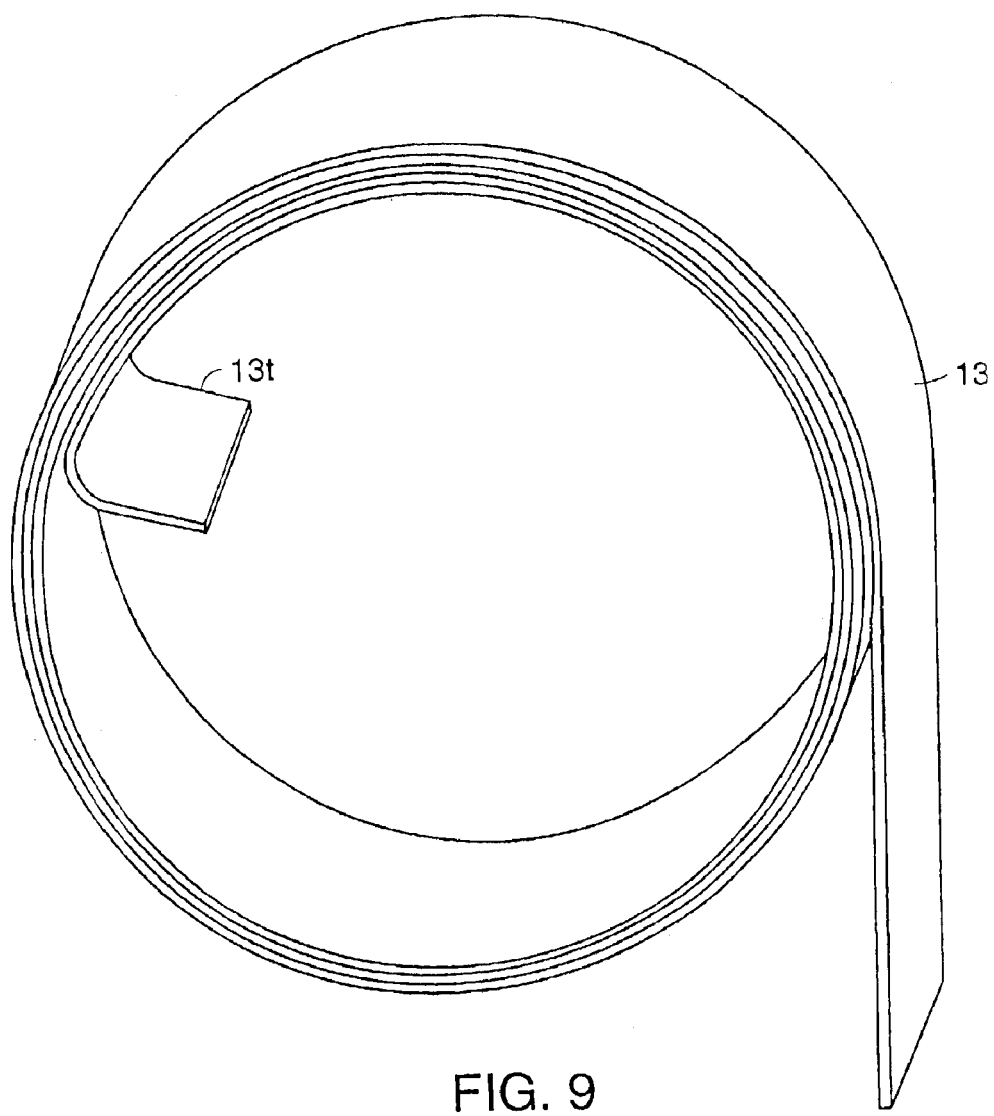
FIG. 9 shows an enlarged view of a resilient element used in a wrap-around manual bone anchor screw placement device.

In the embodiment of the invention shown in FIGS. 4A–D, the resilient element 13 is at least partially wound around the rotatable housing 18, and the rotatable housing 18 and the rotator 14 move as one. The resilient element 13 is secured to the rotatable housing 18 by the insertion of an inwardly projecting tail 13t of the resilient element 13 into a notch 25 in the rotatable housing 18. An enlarged view of the resilient element 13 and inwardly projecting tail 13t is shown in FIG. 9.

Figure 10:
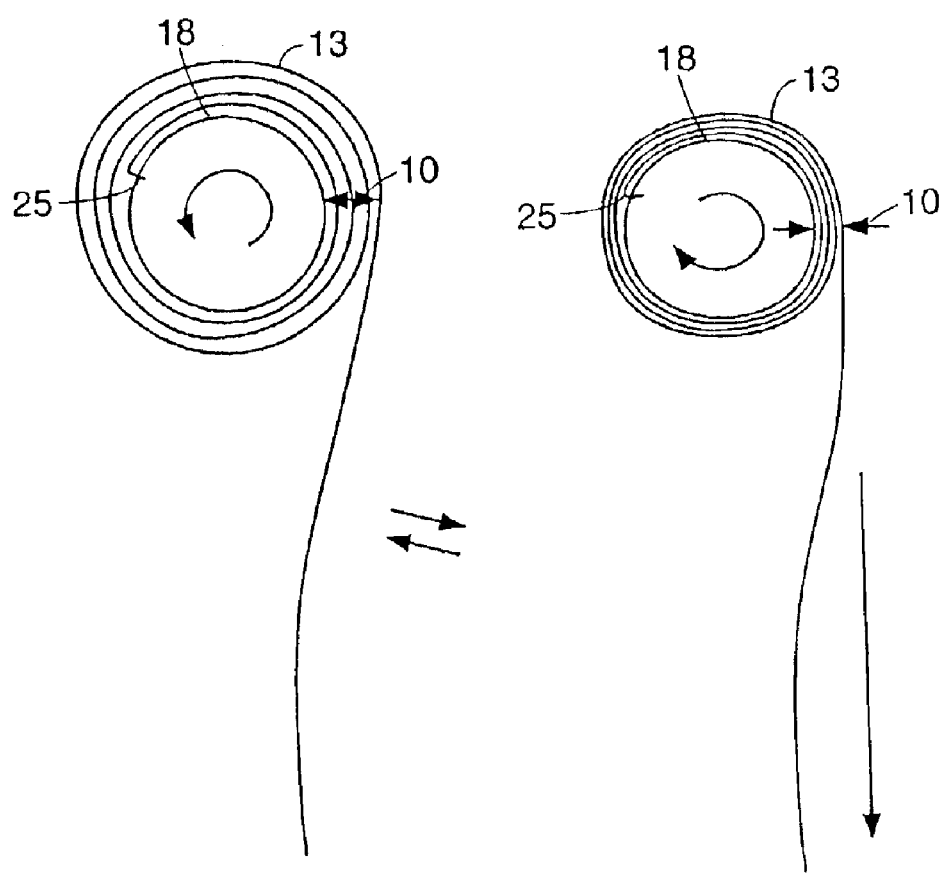
FIG. 10 shows a schematic view of how force is transmitted through the resilient element in a wrap-around manual bone anchor placement device.

As shown schematically in FIG. 10, force transmitted through the resilient element 13 causes the inner diameter ID of the resilient element 13, which is wrapped around the rotatable housing 18 to decrease, and the resilient element 13 to grip the rotatable housing 18, resulting in its rotation. Upon elimination of force on the resilient element 13, the inner diameter ID of the portion of the resilient element 13, wrapped around the rotatable housing 18 gets larger, resulting in free rotation in the opposite direction. The gripping action in one direction and the slipping action in the opposite direction provide the action needed to drive a bone anchor screw 5 into the bone when a linear pull force is exerted on the lever 4.

In the embodiment of the invention shown in FIGS. 4C and 4D, the securing element 166 is positioned at least partially within the rotatable housing 18, and the engaging portion 16 of the securing element 166 rotates in response to the rotation of the rotatable housing 18 and rotator 14.

Figure 5A:
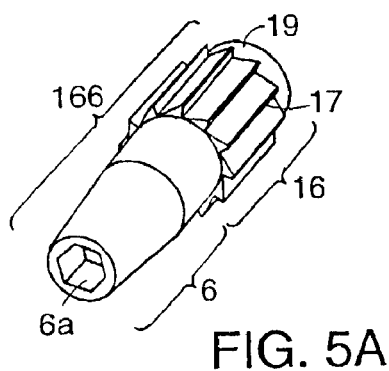
FIGS. 5A–H show enlarged views of securing elements used with a wrap-around manual bone anchor placement device and bone anchor screws according to different embodiments of the invention.
Figure 5B:
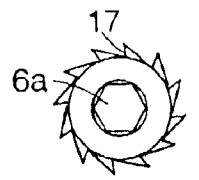
Figure 5C:
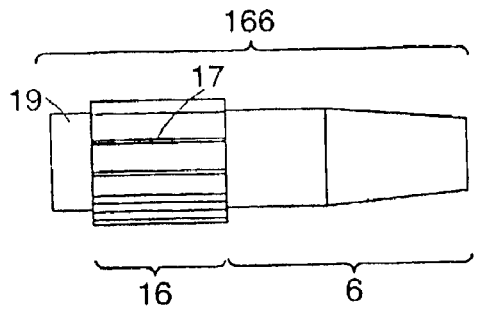
Figure 5D:
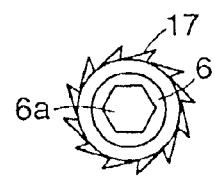
Figure 12D:
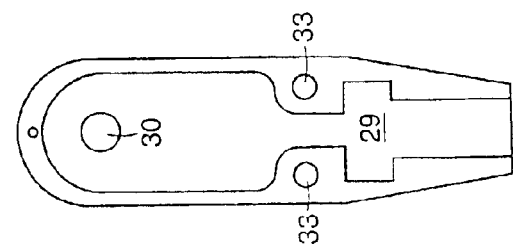
FIGS. 12A–12I show enlarged views of a head module of a wrap-around manual bone anchor placement device according to one embodiment of the invention.
Figure 12C:
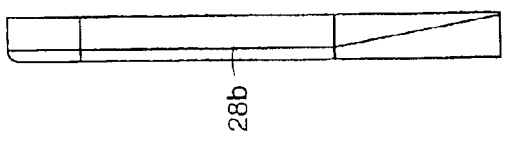
Figure 12A:
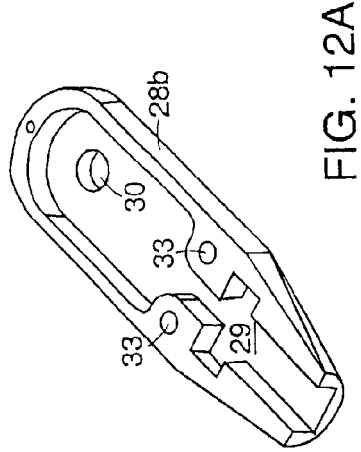
Figure 12B:
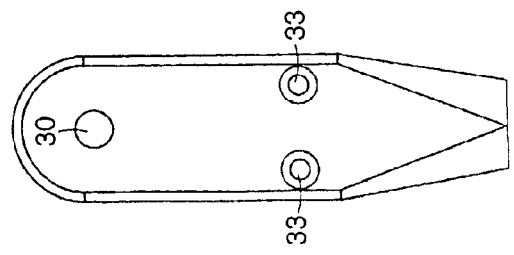
Figure 12I:
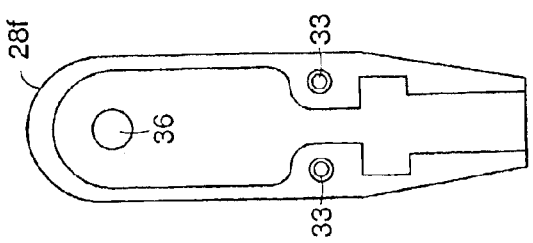
Figure 12F:
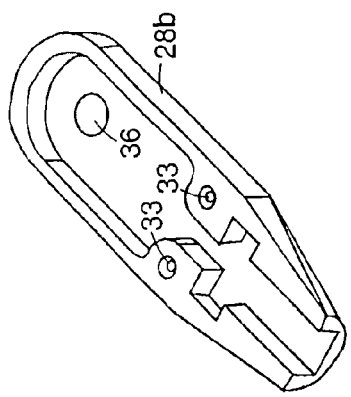

As shown in the enlarged view of the securing element 166 provided in FIGS. 5A and 5C, the securing element 166 further comprises a generally cylindrical front piece 19, which extends from the engaging portion 16 of the securing element and fits into a complementary recessed portion 30 in the inner wall of the head end 3*h* of the shaft portion 3 or the head module 28 (shown in FIGS. 12A, 12B, and 12C). The front piece 19 acts to position the rotatable housing 18 within the head end 3*h* of the shaft 3, or within the head module 28 (as shown in FIGS. 12A–C), allowing it to rotate freely about the axis defined by the front piece 19.

The mating portion 6 of the securing element 166 extends at least partially outside the head end 3*h* of the shaft 3. The bone anchor screw 5 may be seated on the mating portion 6 of the securing element 166 in a variety of ways and the mating portion 6 of the securing element 166 may be fabricated to complement a variety of different types of bone anchor screws 5. In one embodiment of the invention, shown in FIG. 5E, when the bone anchor screw 5 being used provides a shaft 5*a* with a Hex-shape, the mating portion 6 of the securing element 166 is designed to provide a recess 6*a* that has a Hex-shaped cross-section (see FIGS. 5A, B and D). It will be readily apparent to one of ordinary skill in the art that the recess 6*a* of the mating portion 6 of the securing element 166 may be any type of shape (e.g., a T-shape or an X-shape) that allows for frictional and mechanical engagement with a bone anchor screw 5 having a shaft 5*a* with the corresponding shape. In a further embodiment of the invention, shown in FIGS. 5F and 5G, the mating portion 6 of the securing element 166 comprises a shaft 6*b* while the bone anchor screw 5 (shown in FIG. 5H) provides a recess 5*b* complementary to the shape of the shaft 6*b*

Any type of bone anchor screw 5 may be used adaptable to the mating portion 6 of a selected securing element 166. In one embodiment, shown in FIG. 1A, the bone anchor screw 5 has a pre-attached suture 7 and the walls of the shaft 3 defining the head end 3*h* of the shaft have aligned openings 20*a* and 20*b* through which the suture 7 is threaded. (Aligned openings may also be provided in the head module 28 in embodiments of the invention where the bone anchor placement device comprises a head module 28.) Attachment of the suture 7 along the length of the shaft 3 will keep the suture 7 from becoming entangled during the bone anchor screw 5 insertion procedure.

Figure 1B:
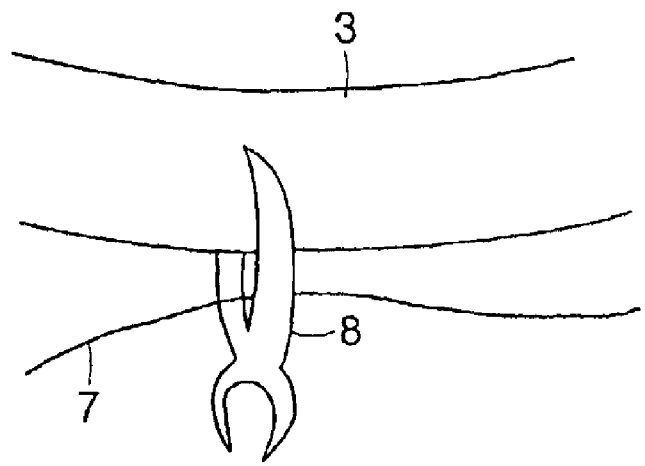
FIG. 1B shows a section of a side-view of the shaft of a manual anchor placement device to which a suture ring is clipped and through which a suture is threaded.
Figure 1C:
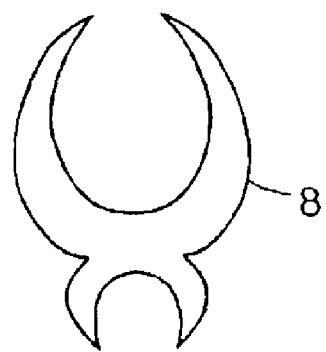
FIG. 1C shows an enlarged cross-sectional view of a suture ring.

In the embodiment of the invention shown in FIGS. 1A–C, the length of the suture 7 extending out of the head end 3*h* of the shaft 3 may be secured by one or more suture rings 8 mounted on the shaft 3. The suture rings 8 may be an integral part of the shaft 3 or may be clipped on as shown in FIG. 1B. After the bone anchor screw 5 is seated, the bone anchor screw 5 disengages from the mating portion 6 of the securing element 166. The suture 7 then slips through aligned openings 20*a* and 20*b* at the head end 3*h* of the shaft 3 and through the suture rings 8, disengaging from the bone anchor placement device 1.

In another embodiment of the invention, shown in FIG. 2, a groove 23 is cut into the outer surface of the handle 2, extending in a line parallel to the longitudinal axis of the shaft 3, which is proximal to the gripping portion 26 of the handle 2. In this embodiment of the invention, the suture 7 is enclosed within a flexible, molded sleeve 24, composed of Teflon® material, for example, which is press-fitted into the groove 23 of the handle 2. In a further embodiment of the invention, a retaining clip 27 may be provided at the end of the sleeve 24 proximal to the gripping portion 26 of the handle 2 to prevent the suture 7 from slipping out before the bone anchor screw 5 is screwed. The user of the manual bone anchor placement device 1 may then cut the retaining clip 27 which allows the suture 7 to slide out of sleeve 24 after the bone anchor 5 is screwed into the bone.

In further embodiments of the invention, the manual bone anchor placement device 1 may be fabricated from modules including a handle module and a shaft module, allowing the user to mix and match different handles 2 with different shafts 3 (including different head assemblies 35). In the embodiment of the invention shown in FIG. 11, the handle module comprises the two halves 2*a* and 2*b* of the handle 2 (including the two halves 26*a* and 26*b* of the gripping portion 26) which are separable from each other. In this embodiment, an old shaft 3*o* may be removed from the handle 2 upon disconnecting the force translator 12 from the connector 11. A new shaft 3*nu* may then be positioned within the handle 2. After connecting the force translator 12 of the new shaft 3*nu* to the connector 11, the two halves 2*a* and 2*b* of the handle 2 are snapped back together and the wrap-around manual bone anchor placement device 1 is ready for use.

Figure 11:
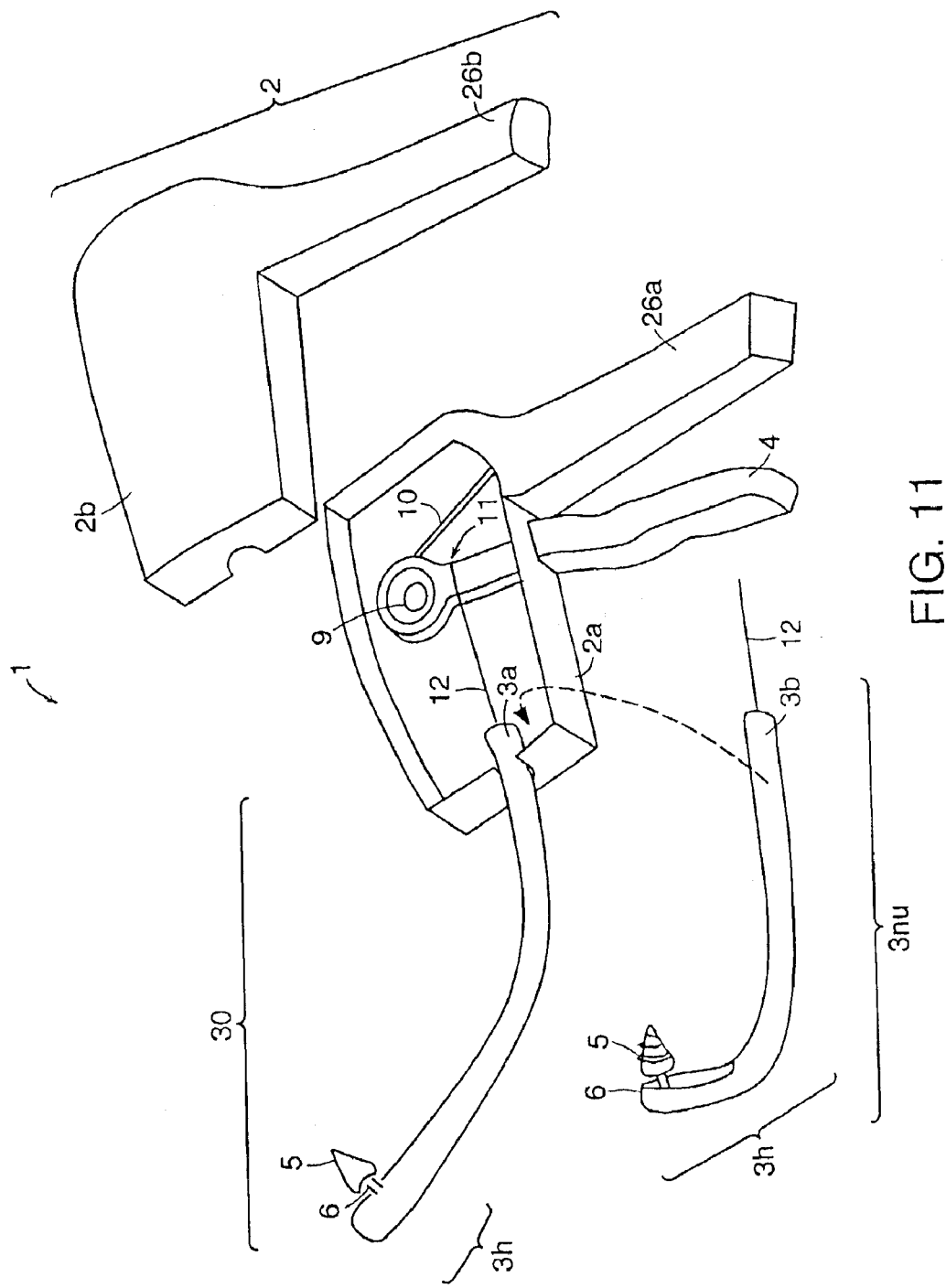
FIG. 11 shows a perspective view of a wrap-around manual anchor placement device according to one embodiment of the invention where the shaft and handle portion comprise interchangeable modules.

In the embodiment shown in FIG. 11, interchanging the old shaft 3*o* from the original bone anchor placement device 1 with shaft 3*nu* provides the user with the opportunity to replace a shaft 3 with an approximately 30 degree upward angle with one with a 90 degree upward angle and a different type of head end 3*h*. The modular nature of the wrap-around bone anchor placement device 1 thus allows users to select the type of shaft 3 or head end 3*h*/head module 28/head assembly 35 that best suits their needs and facilitates repairs of the device 1

As shown in FIGS. 12A–I, the front half 28*f* and back half 28*b* of the head module 28 may also be separated by unscrewing screws at coupling regions 33. This allows the user to vary the exact configuration of the head module 28 and head assembly 35 being used with a particular shaft 3.

Figure 12H:
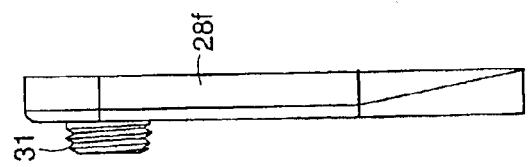
Figure 12E:
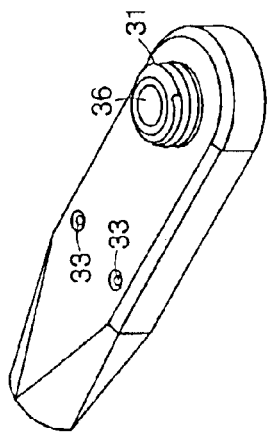
Figure 12G:
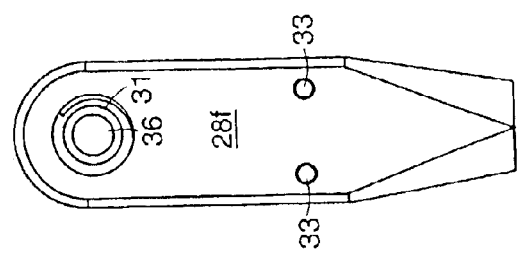
Figure 13A:
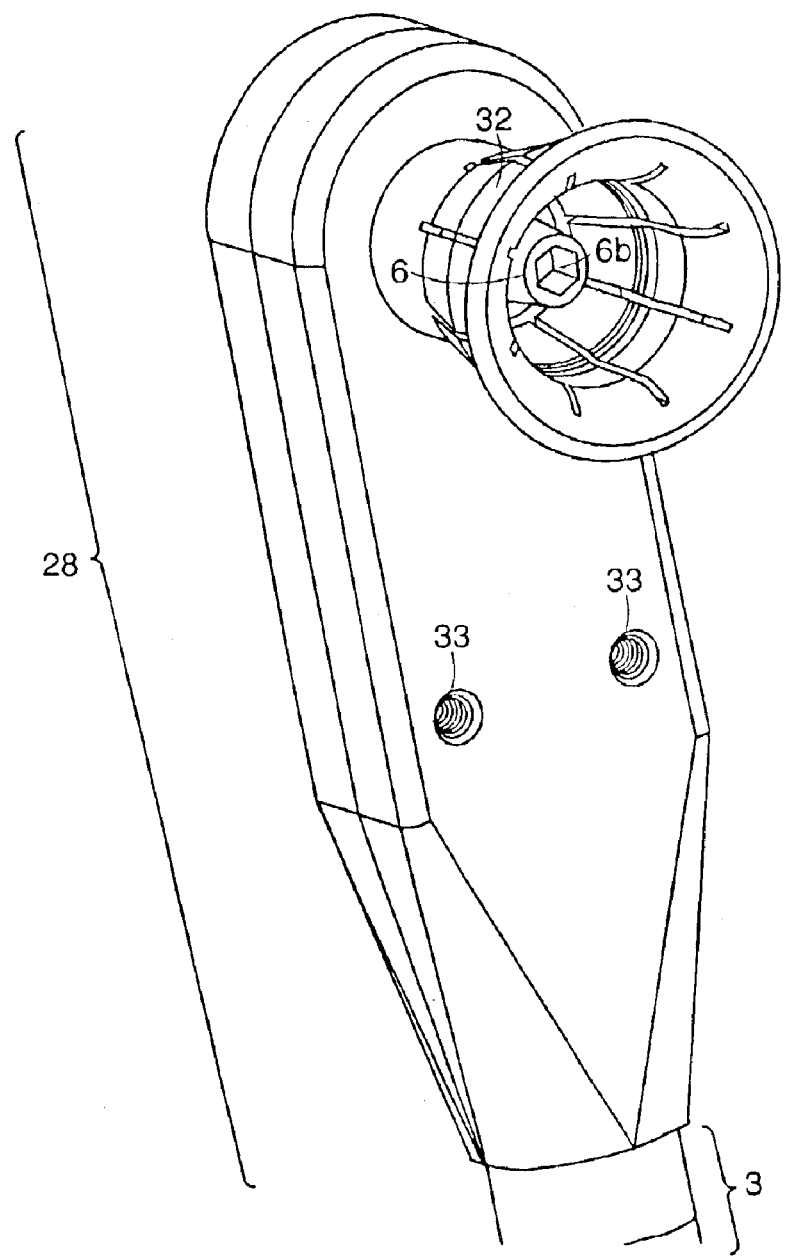
FIG. 13A shows an enlarged perspective view of a head module of a wrap-around manual bone anchor placement device in one embodiment of the invention where a protective sheath is provided to protect the bone anchor screw and the portion of the securing element which protrudes from the head module.
Figure 13B:
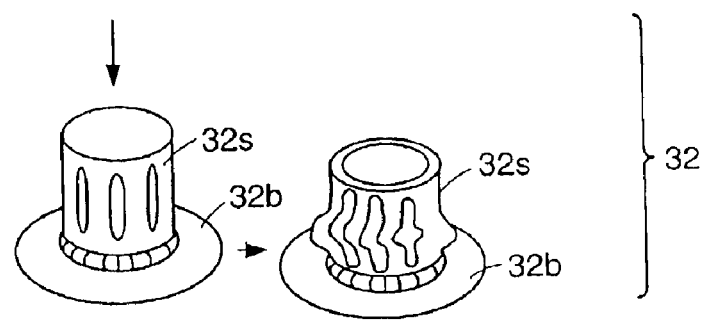
FIG. 13B shows an enlarged perspective view of a collapsible protective cover for a bone anchor screw. The left-hand side of the Figure shows the cover in an uncollapsed state. The right-hand side of the Figure shows the cover in a collapsed state.
Figure 13C:
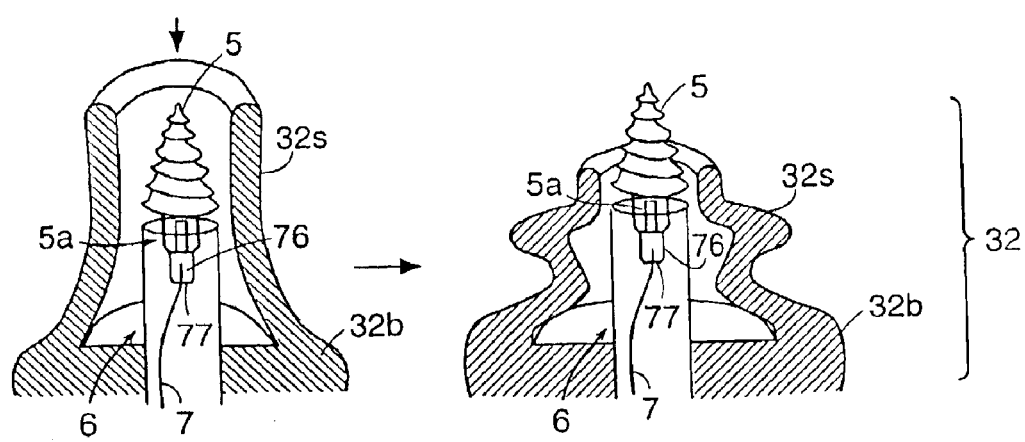
FIG. 13C shows an enlarged cross-sectional view of a collapsible protective cover surrounding a bone anchor screw. The left-hand side of the Figure shows the cover in an uncollapsed state and completely surrounding a bone anchor screw. The right-hand side of the Figure shows the cover in a collapsed state, exposing the bone anchor screw.

In the embodiment shown in FIGS. 12E, 12G, and 12H, the front half of the head module 28*f* may also be provided with a protruding threaded element 31. As shown in FIG. 13A, a protective cover 32 may be seated on this threaded element 31, providing a covering for the bone anchor screw 5 extending outside of the head module through opening 36 and protecting the tip of the bone anchor screw 5 from damage before it contacts a bone insertion site. In a further embodiment of the invention, shown in FIGS. 13B and 13C, the protective cover for protecting a bone anchor screw comprises a base 32*b* for engaging the shaft 3 of the manual bone anchor placement device 1, and a sheath 32*s* coupled to the base 32*b* for surrounding and protecting the bone anchor screw 5. The sheath 32*s* is collapsible and collapses as the bone anchor screw 5 is driven into bone, uncovering the bone anchor screw. Sheath 32*s* materials include flexible plastic, rubber, thin pleated metal, and the like.

Figure 14:
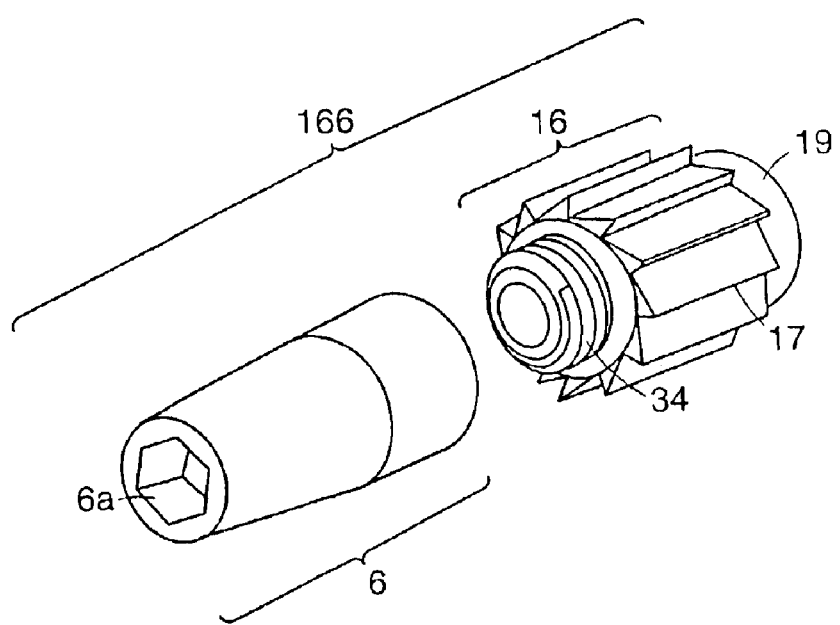
FIG. 14 shows an enlarged version of a securing element used in a wrap-around manual bone anchor placement device according to one embodiment of the invention where the mating portion of the securing element may be uncoupled from the engaging portion of the securing element.

In still a further embodiment of the invention, shown in FIG. 14, the mating portion 6 of the securing element 166 may be uncoupled from the engaging portion 16 of the securing element 166 without opening the head end 3*h* or head module 28. In this embodiment of the invention, the mating portion 6 of the securing element 166 is threaded onto a threaded element 34 which protrudes from the engaging portion 16 of the securing element 166 and which may be unscrewed from the engaging portion 16 of the securing element 166. This embodiment of the invention allows different types of mating portions 6 to be coupled to the engaging portion 16 of the securing element 166 and thus allows the user to select a mating portion 6 of a securing element 166 that is complementary to any desired type of bone anchor screw 5.

Rack and Rotator Manual Bone Anchor Placement Device

Figure 15:
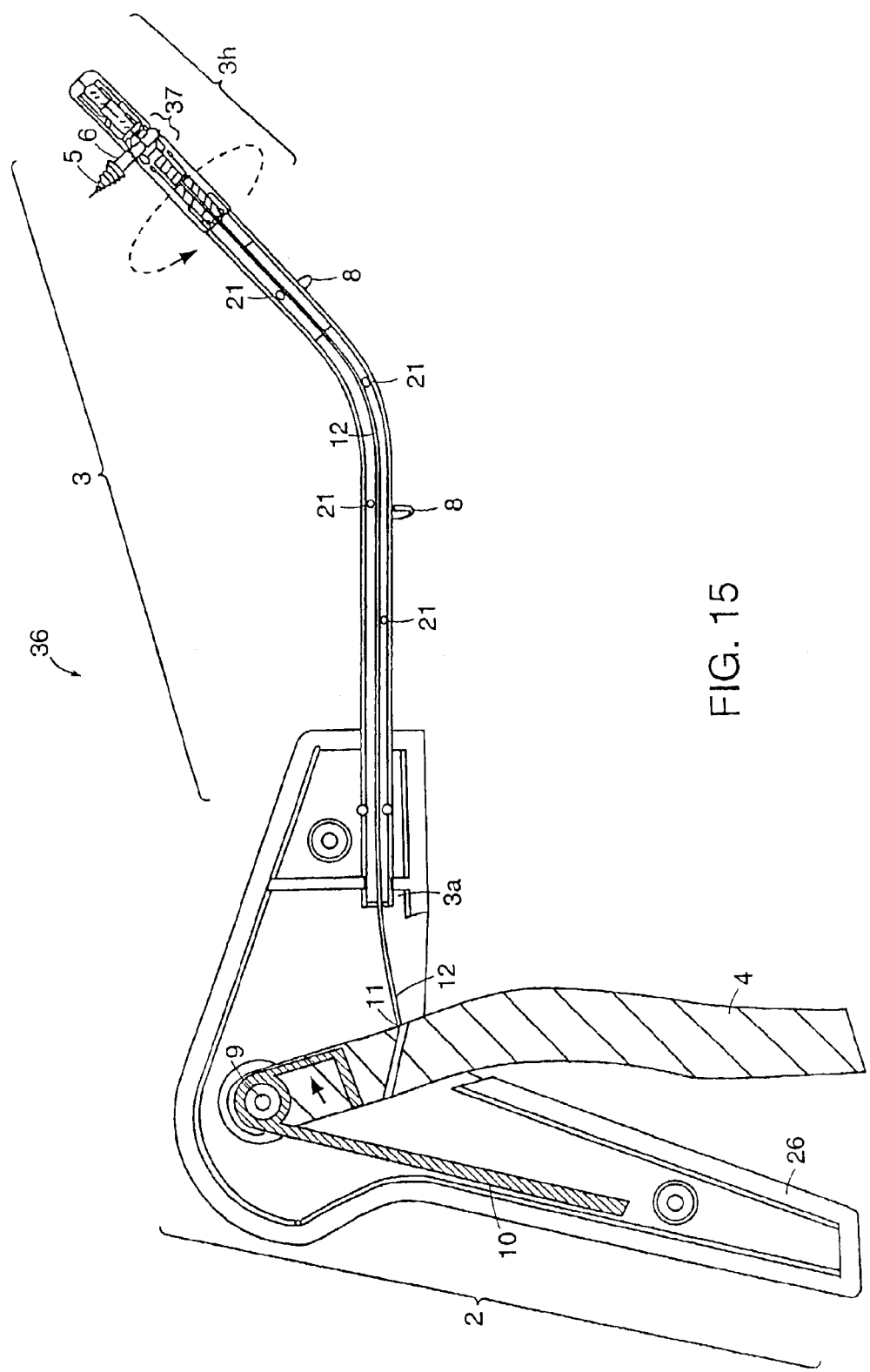
FIG. 15 is a side view of a cross-section through a rack and rotator manual bone anchor placement device according to one embodiment of the invention, showing the components of an action mechanism and a rack and rotator rotary force mechanism.

As shown in FIG. 15, the rack and rotator manual bone anchor placement device 36, like the wrap-around device 1, is substantially pistol- or gun-shaped and comprises a handle 2 and a shaft 3. The handle 2 comprises a gripping portion 26 and a lever 4 through which a user may manually transmit linear force to the rotary force mechanism of the device 36. Like the wrap-around device 1, the shaft 3 of the rack and rotator manual bone anchor placement device 36 comprises a first end 3a proximal to the handle 2, and a second end, or head end 3h, distal to the handle 2.

As in the wrap-around device 1, the shaft portion 3 of the rack and rotator manual bone anchor placement device 36 is curved to facilitate correct placement of the bone anchor placement device 36 to the proper bone anchor screw 5 insertion site, angling upward near its head end 3h. The upward angle can be from 0 to about 90 degrees. In one embodiment of the invention, the upward angle is between about 35 and about 60 degrees. In the embodiment of the invention shown in FIG. 15, the upward angle is approximately 45 degrees. The upward angle of the shaft 3 may be optimized to facilitate insertion of a bone anchor screw 5. The shaft 3 can also be rotated 360 degrees relative to the handle portion 2 (see dashed arrow in FIG. 15).

As in the wrap-around manual bone anchor placement device 1, the rack and rotator manual bone anchor placement device 36 comprise an action mechanism through which force on the lever 4 is transmitted to the force translator 12. The action mechanism comprises lever 4, pivot 9, and the proximal end of the force translator 12. A torsional spring 10 abuts the lever 4 in the handle 2. The force translator 12 is connected to the lever 4 by a connector 11, but the position of the connector 11 relative to the pivot 9 may be varied. As in the wrap-around manual bone anchor device 1, the force translator 12 may be rigid (e.g., a rod) or flexible (e.g., a spring, wire, string, suture material, and the like).

Unlike the wrap-around bone anchor placement device 1, in which a pushing force is transmitted to the force translator 12 by squeezing the lever 4 towards the gripping portion 26 of the handle 2, the rack and rotator bone anchor placement device 36 may be configured so that either a push force or a pull force may be transmitted through the force translator 12 by squeezing the lever 4.

Figure 18A:
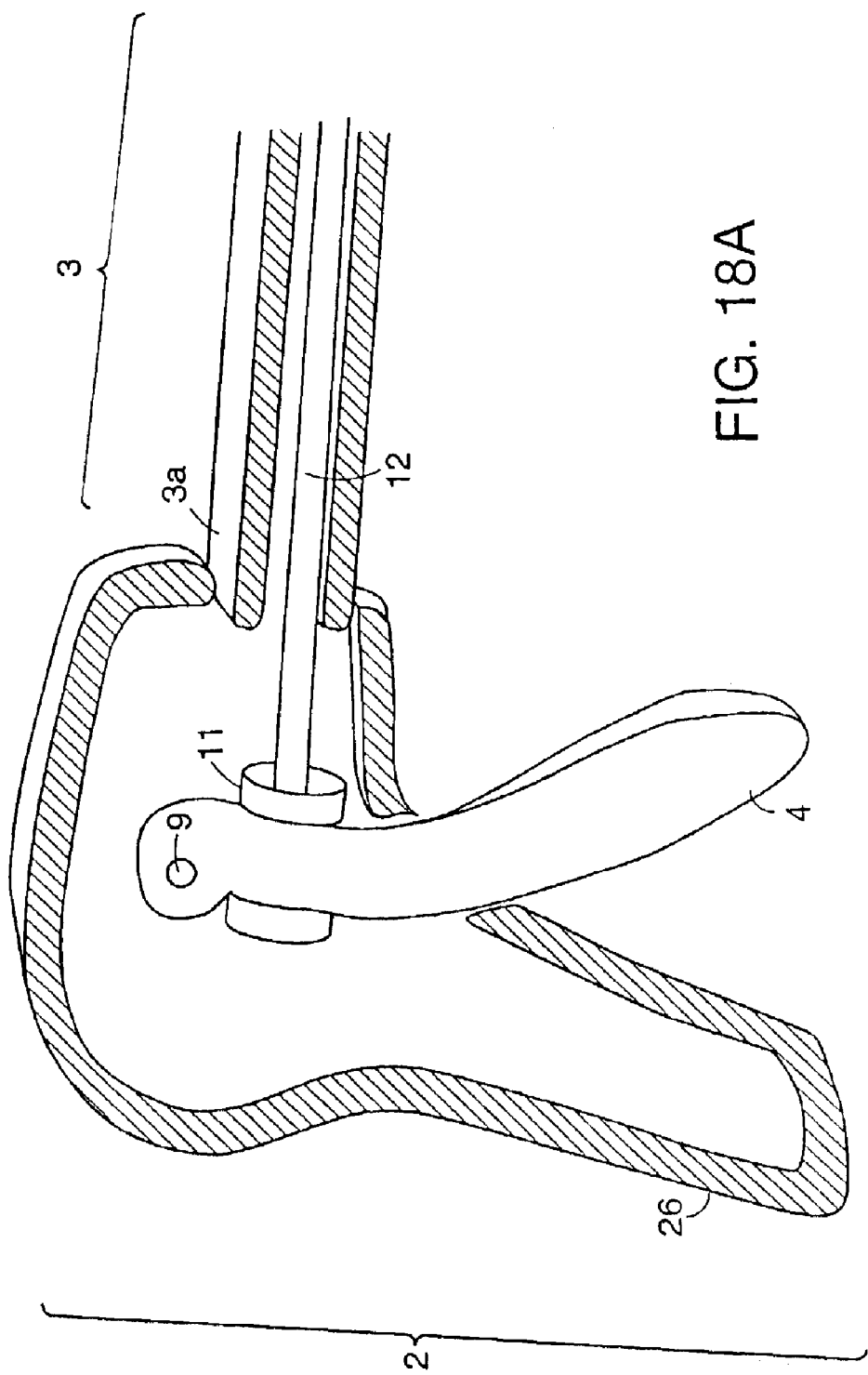
FIGS. 18A and 18B show a side view of a cross-section through the handle and proximal portion of the shaft in a rack and rotator manual bone anchor placement device according to one embodiment of the invention.

In the "pull" embodiment, shown in FIG. 18A, pivot 9 is positioned above connector 11. In this embodiment, mechanical actuation of the lever 4, causes the force translator 12 to be subjected to tensile loading, i.e., a pulling force, when the user squeezes the lever 4 toward the gripping portion 26 of the handle 2, and compressive loading when the user releases the lever 4.

Figure 18B:
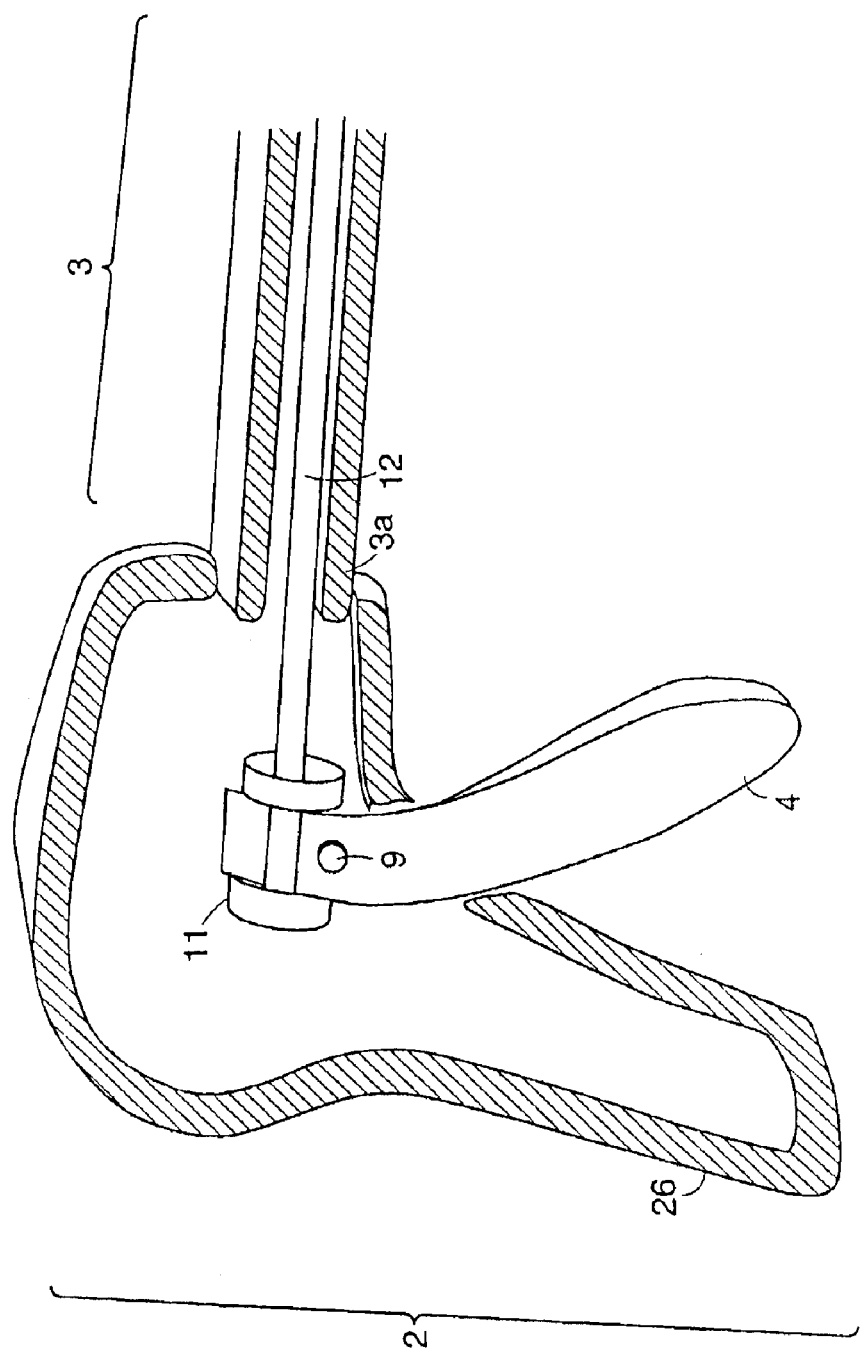

In the "push" embodiment shown in FIG. 18B, pivot 9 is positioned below connector 11 which connects force translator 12 to the lever 4. Squeezing the lever 4 in this embodiment causes the force translator 12 to be subjected to compressive loading, or a pushing force.

Force translator 12 runs through the shaft 3 and transmits linear force exerted manually on the lever 4 to a head assembly 37 positioned at the head end 3h of the shaft 3. Washers 21 positioned on the inside of the shaft 3 reduce the friction caused by the force translator 12 contacting the inside surfaces of the shaft 3 (see FIG. 15).

Head assembly 37 comprises a rack 38, rotator 14 comprising at least one protruding portion 15p, and a coupler 43. Head assembly 37 performs a similar function in the rack and rotator bone anchor placement device 36 as head assembly 35 does in the wrap-around device 1, translating linear force from the force translator 12 to rotary force on a bone anchor screw 5, but does so through a different mechanism.

Figure 16:
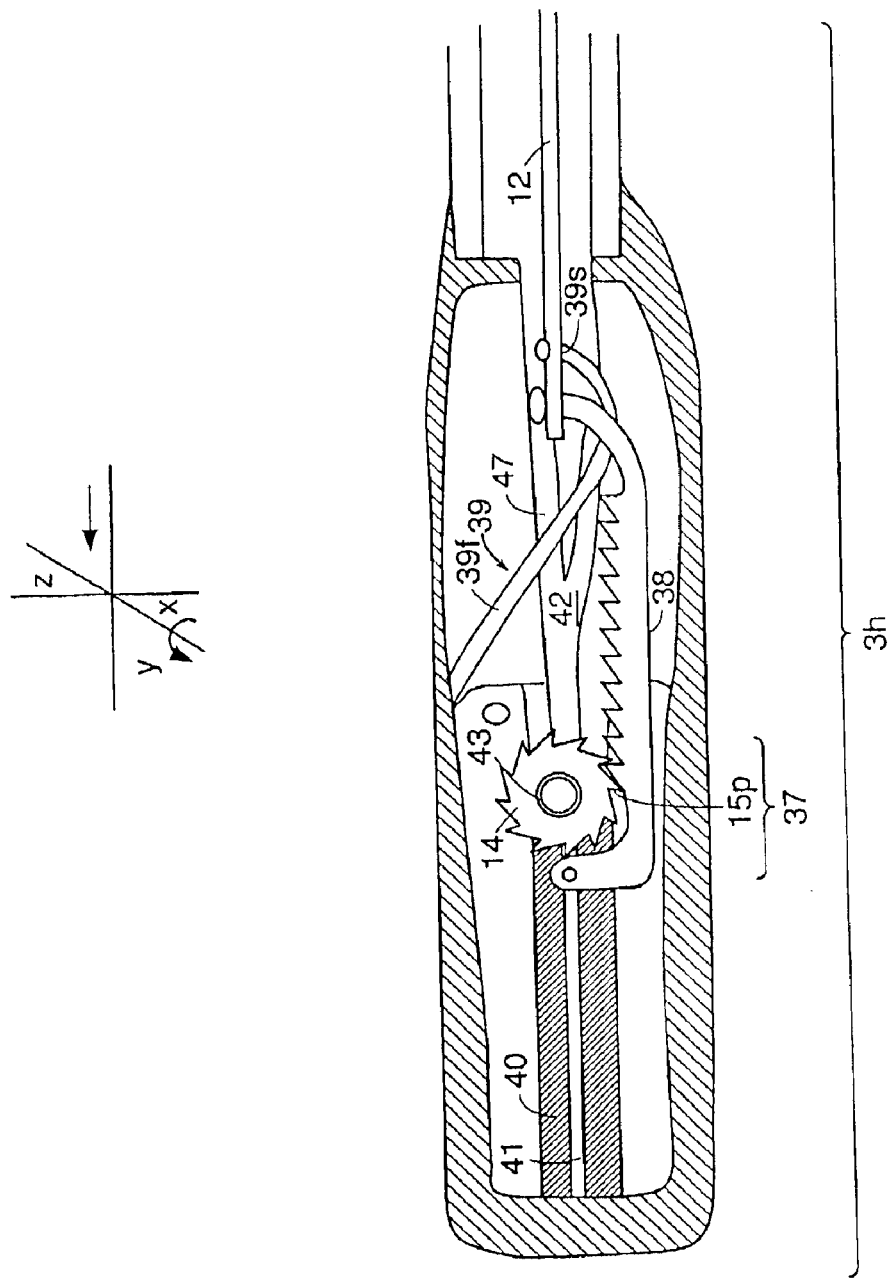
FIG. 16 shows an enlarged view of a head assembly in a rack and rotator manual bone anchor screw placement device in which the rotator comprises a ratchet wheel.

As shown in FIG. 16, the distal end of the force translator 12 is coupled to rack 38 which is positioned proximal to rotator 14. The rack 38 is only able to move in the y direction while the rotator 14 is only able to move rotationally about the x axis. When the rack 38 moves into an engaging position relative to the rotator 14, the teeth of rack 38 mesh with the protruding portion 15p of rotator 14, causing the rotator 14 to rotate. Thus, linear force transmitted through the force translator 12 translates into movement of the rack 38 along the y axis which in turn translates into rotation of the rotator 14 about the x axis. The rotator 14 is coupled to coupler 43 which is capable of mating with, or engaging, a bone anchor screw 5. Rotation of the rotator 14 is translated into a torque applied on the coupler 43, which in turn drives, or screws, a bone anchor screw 5 into bone. Rotators 14, which may be used with racks 38 of the present invention, include ratchet wheels, pawls, pinions, gears, and the like.

In the embodiment of the invention shown in FIG. 16, the rotator 14 comprises a ratchet wheel. In this embodiment of the invention, the interior of the head end 3h of the shaft 3 comprises a grooved element 40 which includes an actuating groove 41 and a return groove 42. A head assembly spring 39 is also positioned within the head end 3h and is coupled by a first end 39f to the inner wall of the head end 3h of the shaft 3 distal to rack 38 and at a second end 39s to force translator 12. Squeezing lever 4 exerts a linear pull force on the translator 12 which mechanically pulls the rack 38 along the actuating groove 41 towards the rotator/ratchet wheel 14. When the rack 38 reaches an engaging position it engages the protruding portions 15p of the rotator/ratchet wheel 14 and rotates the rotator/ratchet wheel 14, which in turn rotates coupler 43. Coupler 43 engages, or mates with, a bone anchor screw 5, and rotation of the coupler 43 applies a torque on the bone anchor screw 5, thereby screwing it into bone.

Release of lever 4 by the operator transmits a compressive force through the force translator 12 (in this embodiment, a flexible wire) to the head assembly spring 39. A push force exerted by head assembly spring 39 in response to this compressive force forces the rack back into return groove 42 during the return stroke and disengages the rack 38 from the rotator 14.

The rack and rotator rotary force mechanism shown in FIG. 16 may also be adapted for a push embodiment. In a push embodiment, compressive loading on the force translator 12 forces the rack 38 forward to engage the rotator/ratchet wheel 14 which rotates in response to this engagement. The rotation of the rotator/ratchet wheel 14 rotates coupler 43, which in turn applies torque on a bone anchor screw 5. By varying the position of the connector 11 relative to the pivot 9 in the action mechanism as shown in FIGS. 18A and 18B, the device 36 may be configured to be used in either a pull or push embodiment.

Figure 17:
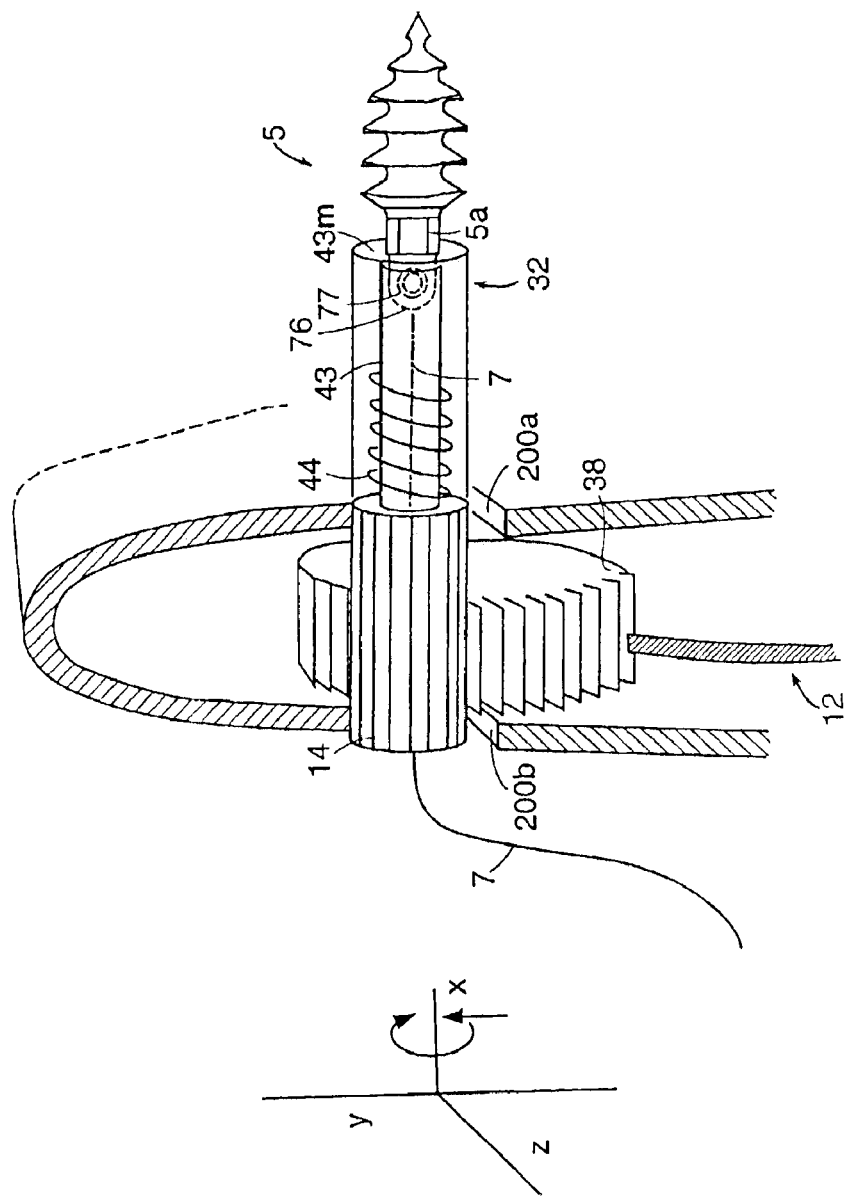
FIG. 17 shows an enlarged view of a head assembly in a rack and rotator manual bone anchor placement device in which the rotator comprises a pinion.

In the embodiment of the invention shown in FIG. 17, the rotator 14 comprises a pinion. Rotary motion from the rotator/pinion 14 is transmitted to a bone anchor screw 5 through coupler 43 which extends at least partially through the head end 3h of the shaft 3 through opening 200a. A push force or a pull force may be transmitted through the force translator 12, as discussed above, by varying the position of the connector 11 relative to the pivot 9 in the action mechanism of the device 36. A rotator spring 44 provides an opposing force to return the rotator/pinion 14 to its original position. In the embodiment of the invention shown in FIG. 17, the bone anchor screw 5 is pre-attached to a suture 7, and both the coupler 43 and the rotator/pinion 14 have openings through which the suture 7 is threaded. The suture 7 dangles from the head end 3h of shaft 3 through opening 200b.

Figure 19:
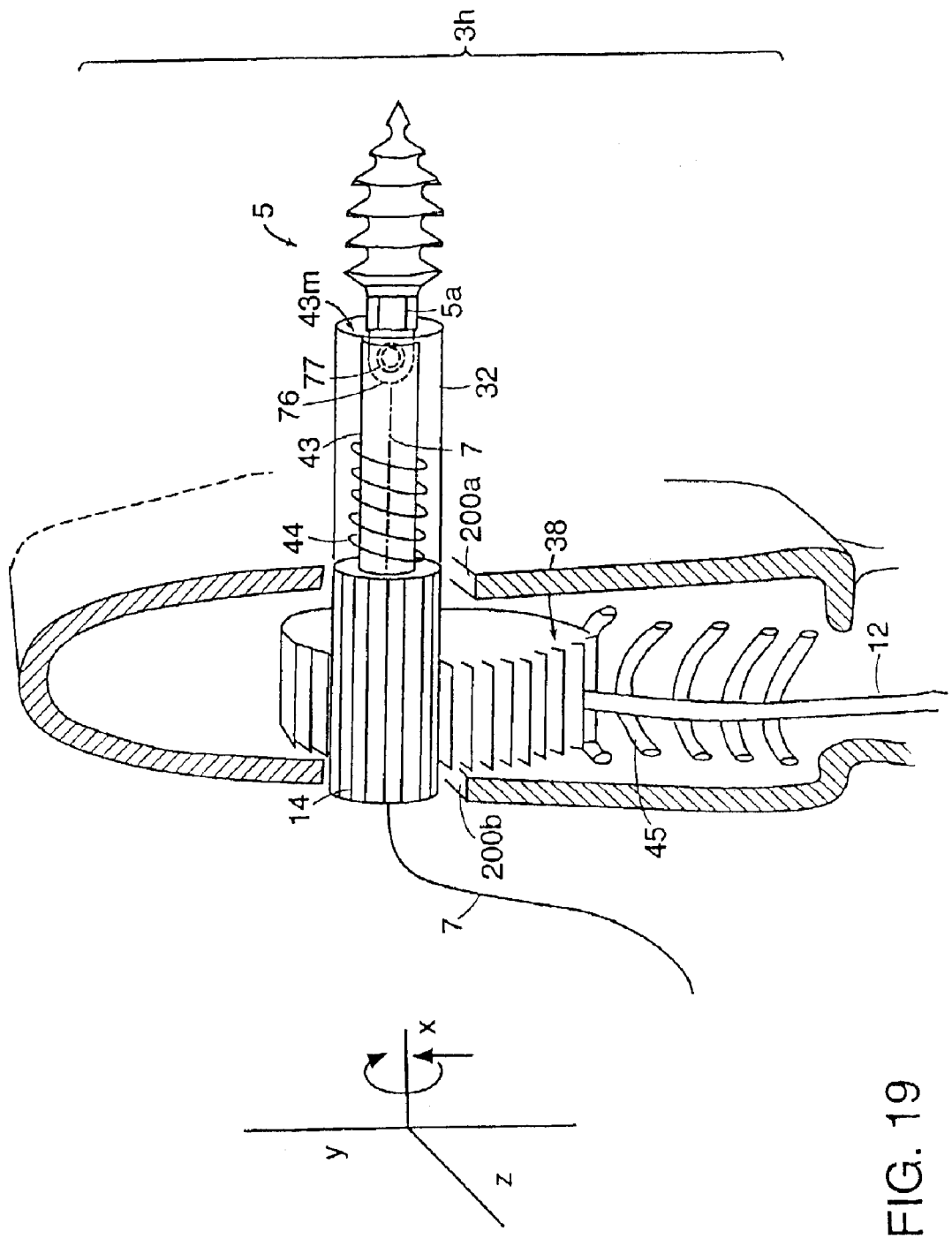
FIG. 19 shows an enlarged cross-sectional view of a head assembly in a rack and rotator manual bone anchor placement device according to one embodiment of the invention, in which linear force is transmitted to the rack through a rack spring and the rotator comprises a pinion. A bone anchor screw pre-attached to a suture is shown coupled to the pinion by a coupler. The bone anchor screw is covered by a protective cover. The portion of the bone anchor screw and pre-attached suture inside the coupler is shown by dashed lines in the Figure.

FIG. 19 shows an embodiment of the invention in which the rotator 14 is a pinion, and a compressive force, or push force, is transmitted on a force translator 12. An opposing compressive force is provided by rack spring 45, shown in cross-section in the Figure, which encircles the end of the force translator 12 proximal to rack 38 and forces the rack 38 back to its original position during a release stroke.

Figure 20:
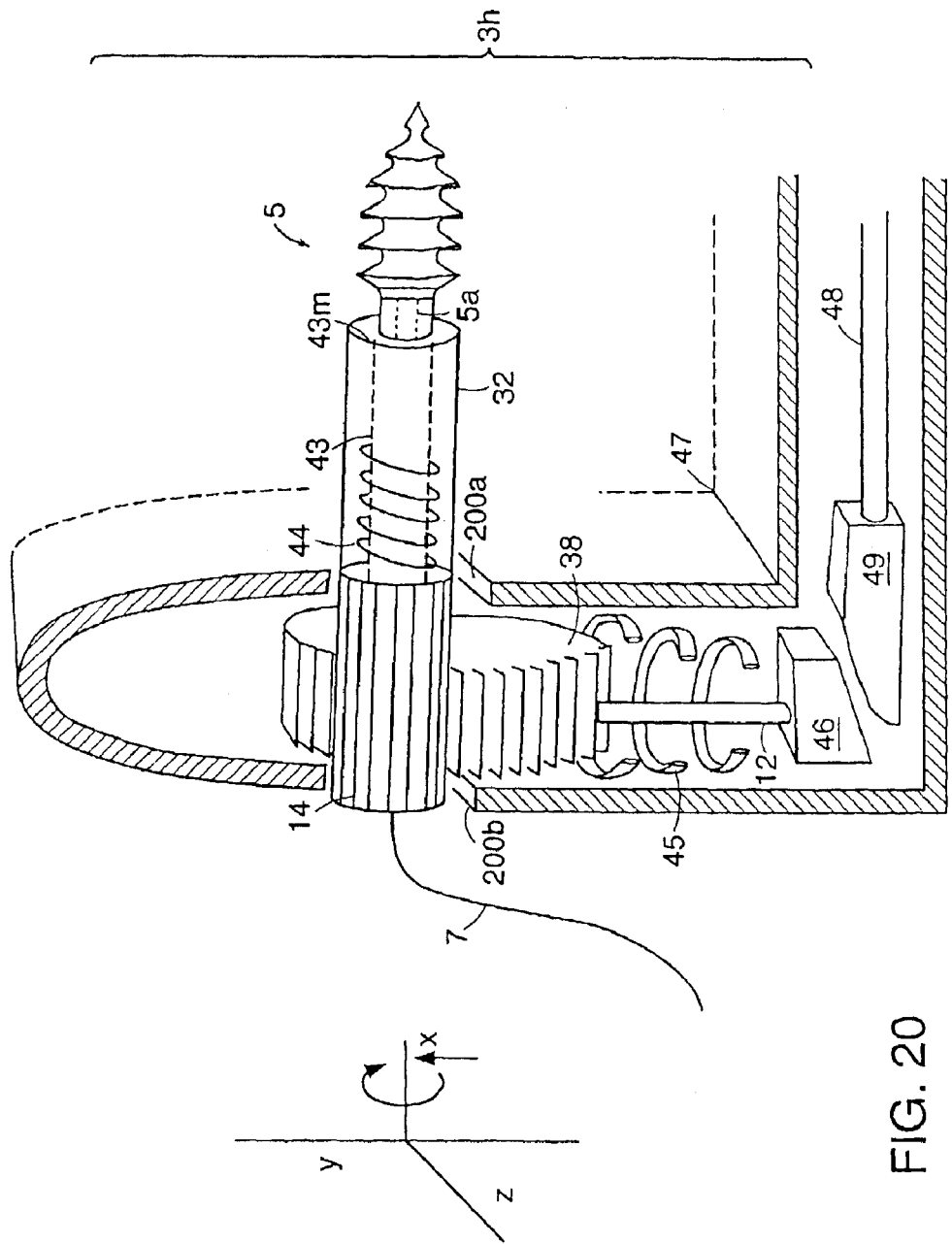
FIG. 20 shows an enlarged cross-sectional view of a head assembly in a rack and rotator manual bone anchor placement device according to one embodiment of the invention in which linear force is transmitted to the rack via wedge members.

FIG. 20 shows a further embodiment of the invention in which the force translator 12 includes a first wedge member 46 at the end of the force translator 12 distal to the rack 38. In this embodiment, the force translator 12 is not directly coupled to the lever 4, but terminates substantially at the neck 47 of the head end 3h of the shaft 3. The translator 12 receives force from a tubular member 48 which terminates in a second wedge member 49 and which is connected to the lever 4 at connector 11. Actuation of the lever 4 pushes the second wedge member 49 against the first wedge member 46 and transmits a compressive force, i.e., a push force, to the force translator 12. During the release stroke, rotator spring 44 forces the rotator/pinion 14 back to its original position while rack spring 45 forces the rack 38 into its initial position.

Figure 21:
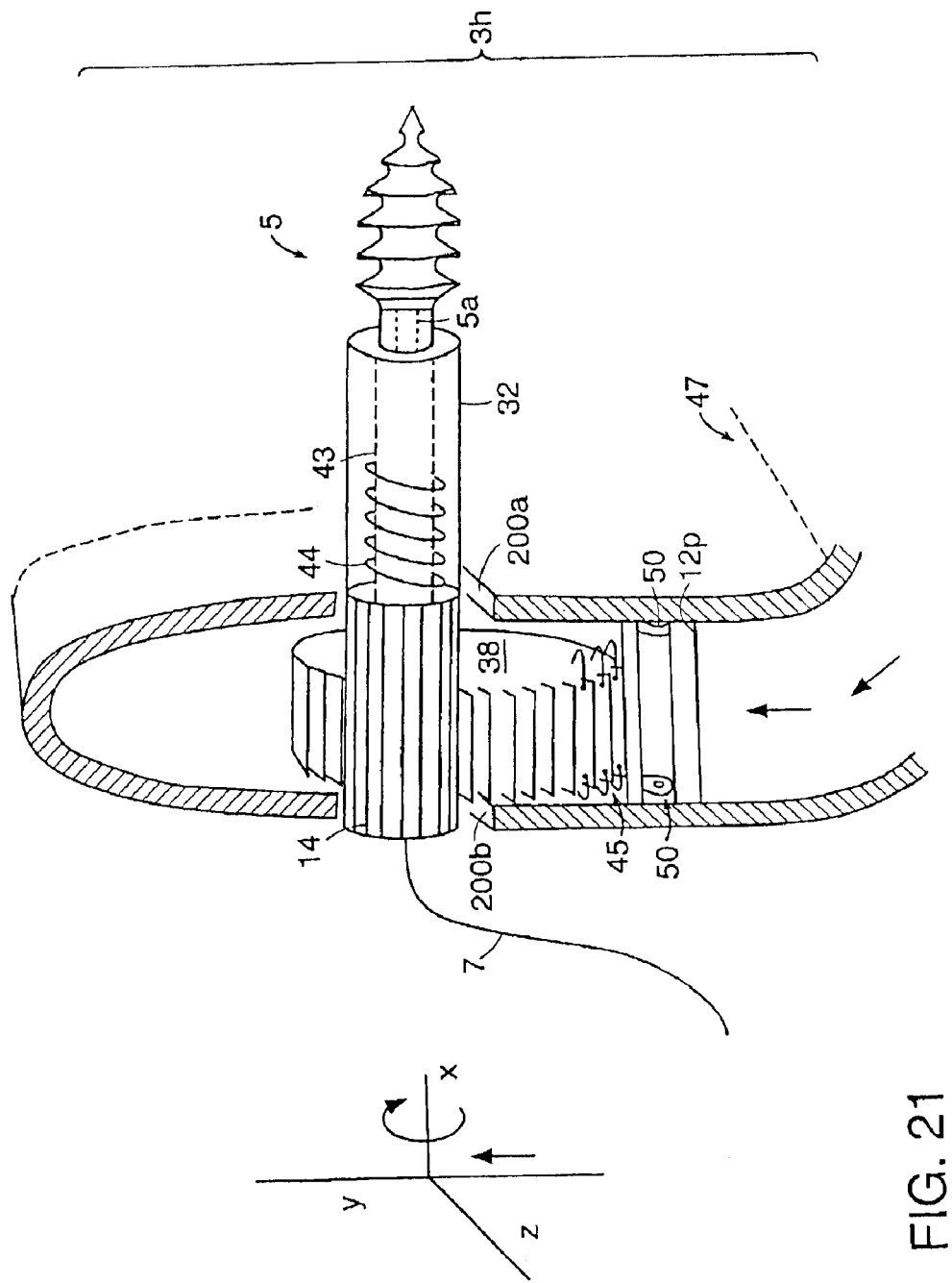
FIG. 21 shows an enlarged cross-sectional view of a head assembly in a rack and rotator manual bone anchor placement device according to one embodiment of the invention in which linear force is transmitted to the rack by pneumatic or hydraulic force on a plunger.

FIG. 21 shows a further embodiment of the invention in which hydraulic or pneumatic pressure is used to exert a compressive, or push force, on a force translator 12p. In this embodiment of the invention, the force translator 12p is a plunger which is positioned in close proximity to the rack 38. An O ring 50 maintains a seal separating air or fluid in the shaft 3 from the rack 38 and rotator/pinion 14 assembly. Hydraulic or pneumatic forces forced through the shaft 3 upon actuation of the lever 4 drive the plunger 12p forward, transmitting linear force from the plunger 12p to the rack 38, which is in turn pushed forward to engage the rotator/pinion 14. The rotator/pinion 14 rotates and transmits rotary force to coupler 43, which applies a torque to a bone anchor screw 5. Opposing compression forces from rotator spring 44 forces the rotator/pinion 14 back to its original position while rack spring 45 forces the rack 38 to return to its initial position.

As will be readily apparent to those of ordinary skill in the art, many of the features of the wrap-around manual bone anchor placement device 1 may be adapted for use with the rack and rotator manual bone anchor placement device 36. For example, a suture 7 pre-attached to a bone anchor screw 5 may be clipped to the shaft 3 by suture rings 8 to keep the suture 7 from becoming entangled during the bone anchor screw 5 insertion procedure. Alternatively, the suture 7 may be enclosed within a flexible, molded sleeve 24 press-fitted into a groove 23 cut into the handle 2. A retaining clip 27 provided at the end of the sleeve 24 proximal to the gripping portion 26 of the handle 2 may be provided to prevent the suture 7 from slipping out of the sleeve 24 before the bone anchor screw 5 is screwed into bone.

Figure 5E:
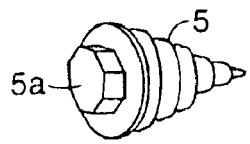
Figure 5F:
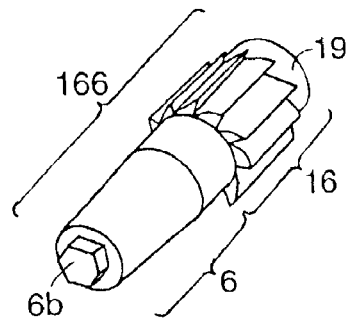
Figure 5G:
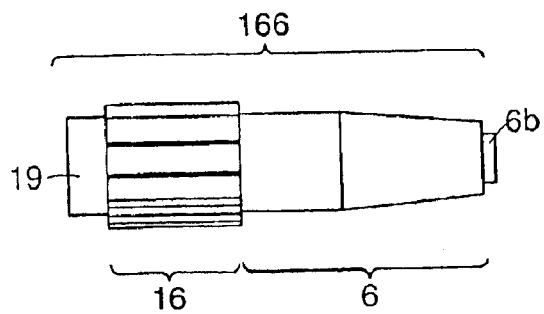
Figure 5H:
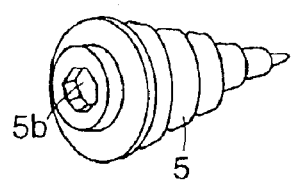

The coupler 43 may also be configured to be adapted to a wide variety of bone anchor screws 5. Like the securing element 166 of the wrap-around bone anchor placement device 1, the coupler 43 of the rack and rotator manual bone anchor placement device 36 comprises a mating portion 43m, which extends at least partially outside head end 3h of the shaft 3 and which can be fabricated to complement different types of bone anchor screws 5. In the embodiment of the invention shown in FIG. 19, the coupler 43 provides a mating portion 43m, which is a Hex-shaped recess and which seats a bone anchor screw 5 with a Hex-shaped shaft 5a, (e.g., as shown in FIG. 5E). The mating portion 43m of the, coupler 43 may be configured in any type of shape (e.g., shaft or recess) that allows for frictional and mechanical engagement with a bone anchor screw 5 having the corresponding shape (e.g., recess or shaft).

As with the wrap-around manual bone anchor placement device 1, a protective cover 32 may be provided to protect the tip of the bone anchor screw 5 from damage before it contacts a bone insertion site, and may be collapsible, to expose the bone anchor screw 5 only when it contacts the bone.

As with the wrap-around manual bone anchor placement device 1, the rack and rotator bone anchor placement device 36 may be fabricated in a modular configuration to provide for the ready interchange of different head modules and shaft modules. For example, a shaft 3 which comprises a rack 38 and rotator 14 head assembly 37 may be interchanged with a shaft 3 comprising the same type of head assembly 37, but with a different angle of curvature. Alternatively, a shaft 3 with a rack 38 and rotator 14 head assembly 37 may be interchanged with a shaft 3 comprising wrap-around head assembly 35. Similarly, different couplers 43 may be interchanged to facilitate the use of different bone anchor screws 5.

Cup and Washer Manual Bone Anchor Placement Device

As with the previously disclosed manual bone anchor placement devices 1 and 36, the cup and washer manual bone anchor placement device 52, is configured to be substantially pistol- or gun-shaped, having a handle 2 with a gripping portion 26 and a lever 4. In the cup and washer manual bone anchor placement device 52, however, the "barrel of the gun" is formed by a driver rod 53 which extends through the handle 2 and is substantially perpendicular along its length to the longitudinal axis of the gripping portion 26 of the handle 2.

Figure 22A:
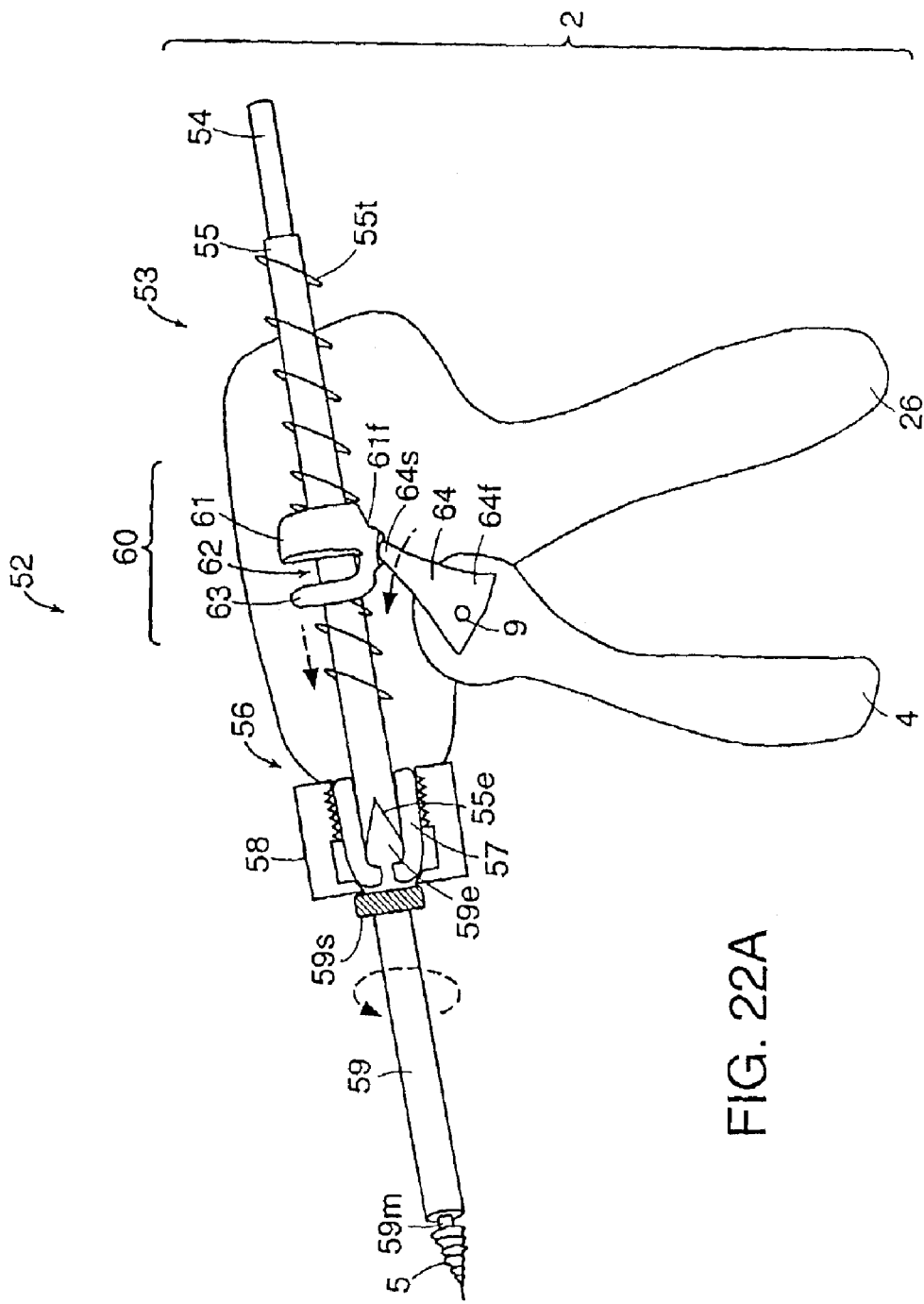
FIG. 22A shows a cross-sectional side-view of a cup and washer manual bone anchor placement device according to one embodiment of the invention which comprises a cup and washer rotary force mechanism.
Figure 22B:
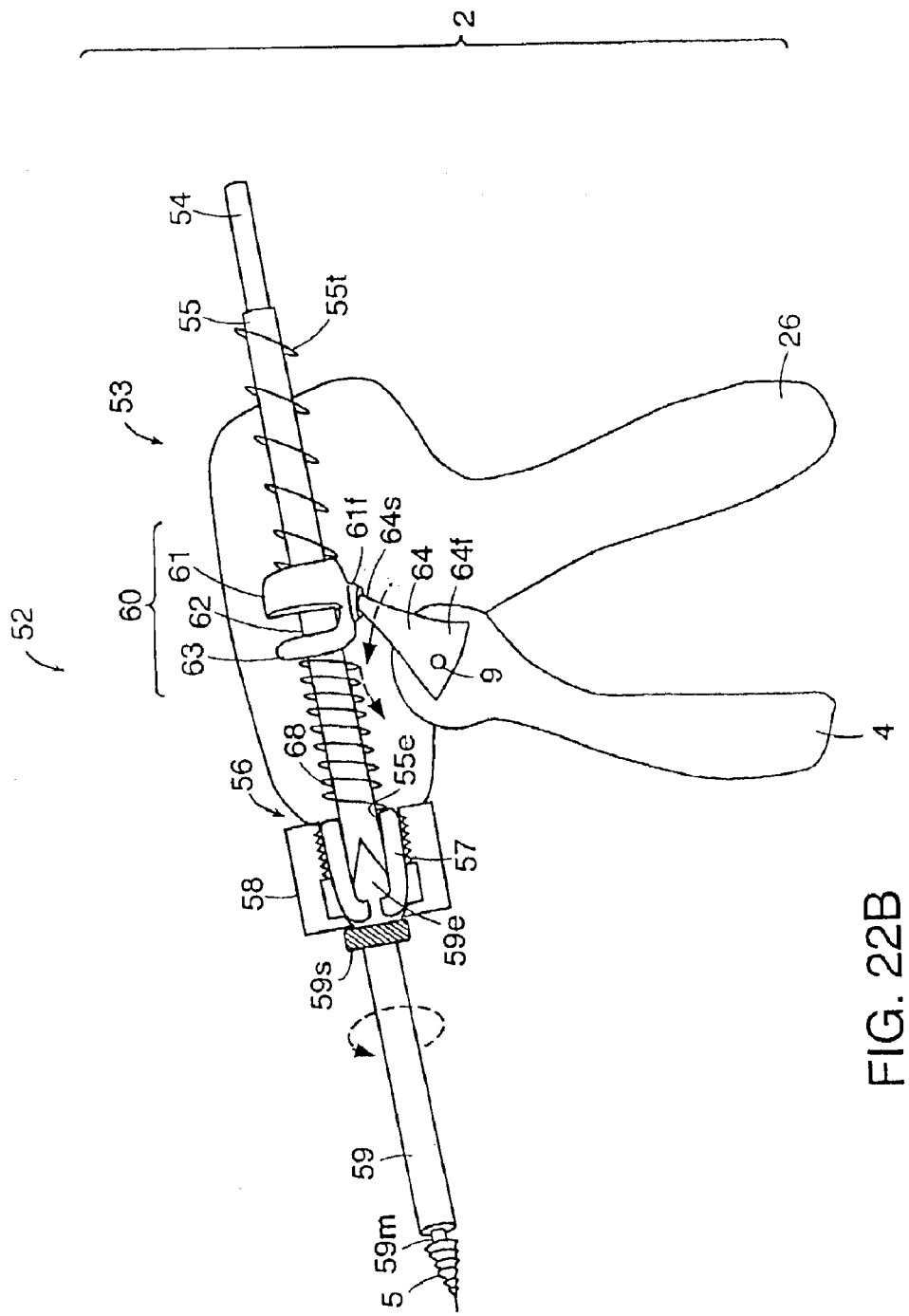
FIG. 22B shows a further embodiment of the invention in which a return coil spring is provided between the cup and washer assembly and the barrel end of the handle.

FIGS. 22A and 22B show a cross-section of the cup and washer manual bone anchor placement device 52. The driver rod 53 comprises a smooth portion 54 and a lead screw portion 55 with integral single or multistart threads 55t. The lead screw portion 55 may be integral with the smooth portion 54. Alternatively, the lead screw portion 55 may be screwed onto threads or grooves at one of the ends of the smooth portion 52. The lead screw portion 55 may extend from one end of the handle 2 to the other end of the handle 2 or the lead screw portion 55 may comprise a substantial portion of the driver rod 53. As used herein, "a substantial portion" refers to greater than 50% of the length of the driver rod 53. In a different embodiment of the invention, the driver rod 53 may comprise a flat stock twisted into a spiral with a long pitch.

The lead screw portion 55 of the driver rod 53 further comprises an engaging element 55e at the end of the lead screw portion 55 distal to smooth portion 52 of the driver rod 53. The engaging element 55e engages with a coupling member 59. The coupling member 59 comprises a mating portion 59m for mating with a bone anchor screw 5 and an engaging portion 59e for engaging with the engaging element 55e of the lead screw portion 55.

The position of the coupling member 59 relative to the lead screw portion 55 of the driver rod 53 may be controlled by means of a coupling member stop 59s. A chuck 57 provided at the barrel end 56 of the handle 2 further secures coupling member 59 to the lead screw portion 55 of the driver rod 53. Since the chuck 57 contacts both the lead screw portion 55 of the driver rod 53 and the coupling member 59, any force transmitted through the driver rod 53 is also transmitted through the coupling member 59 to the bone anchor screw 5. In a further embodiment of the invention, a rotatable twist lock 58 is provided, thereby supplying an additional means of securing the chuck 57 to coupling member 59.

The rotary force mechanism in the cup and washer manual bone anchor placement device 52 comprises cup and washer assembly 60, which includes a cup 61, a washer 62, and at least one engaging pin 65. The cup 61 is capable of axial movement along the lead screw portion 55 of the driver rod 53, while the washer 62 is capable of both axial motion and rotational motion along the lead screw portion 55.

Movement of the cup 61 is controlled by actuation of an action mechanism, which comprises a lever 4 and a force translating member 64. The force translating member 64 comprises a first end 64f and a second end 64s. The first end 64f of the force translating member 64 is coupled to the lever 4 at pivot point 9 while the second end 64s is coupled to the side of the cup 61 by means of flanges 61f on the cup. The flanges 61f form a yoke, which links the cup 61 to the force translating member 64. The cup 61 is thus free to ride on the lead screw 55 in response to movement of force translating member 64.

Figure 23A:
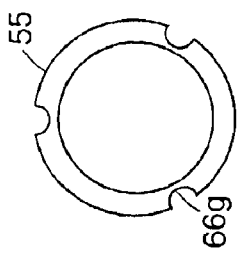
FIGS. 23A–D show an enlarged views of a cup and washer assembly used in a cup and washer manual bone anchor placement device according to one embodiment of the invention.
Figure 23B:
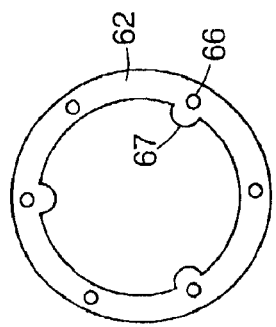
Figure 23C:
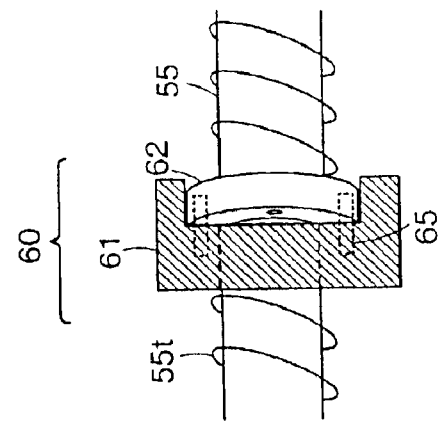
Figure 23D:
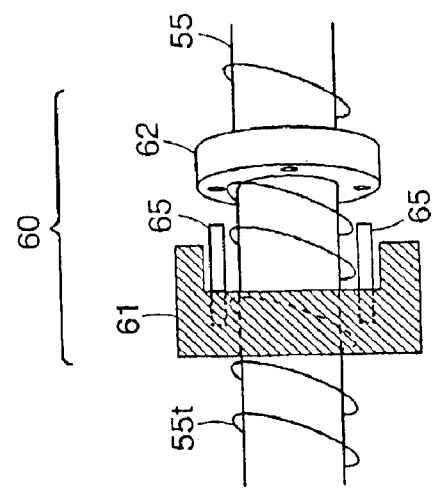
Figure 24A:
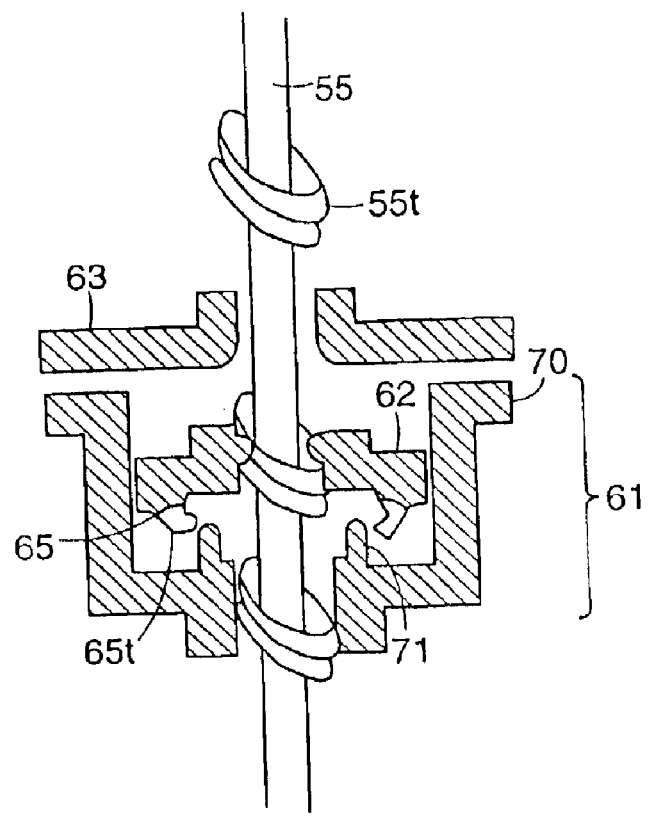
FIGS. 24A and 24B show an enlarged view of a cup and washer assembly according to one aspect of the invention.
Figure 24B:
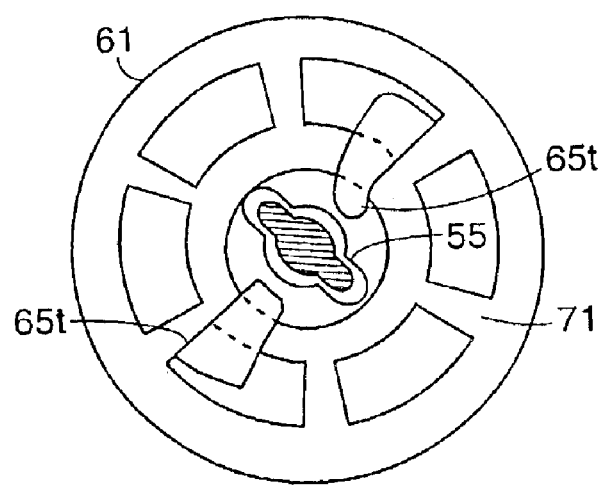
Figure 25A:
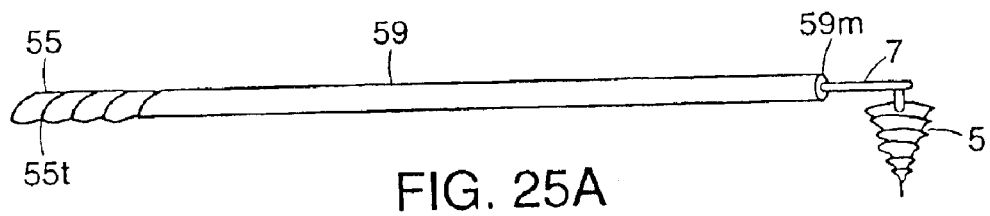
FIG. 25A shows a section of a lead anchor screw and a coupling element used in a cup and washer manual bone anchor placement device according to one embodiment of the invention in which the coupling element comprises a recess through which the suture of a bone anchor screw is threaded. The Figure shows the suture partly pulled out of the recess.
Figure 25B:
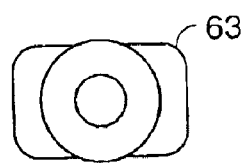
FIG. 25B shows a perspective view of the top of a cover plate used in a cup and washer assembly according to one embodiment of the invention.
Figure 25C:
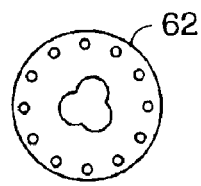
FIG. 25C shows a perspective view of the top of a washer used in a cup and washer assembly.
Figure 25D:
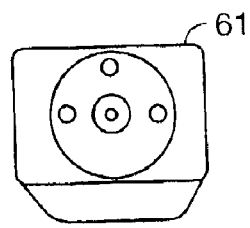
FIG. 25D shows a perspective view of the top of a cup used in the cup and washer assembly (i.e., the side which faces the washer).

The cup and washer manual bone anchor placement device 52 operates on the principle of a child's top. Applying a linear force on the lever 4 by squeezing it towards the gripping portion 26 of the handle 2 actuates the action mechanism. Linear force is transmitted from the lever 4 to the force translating member 64 and is transmitted to cup 61. In the embodiment of the invention shown in FIG. 23, the cup 61 comprises two engaging pins 65 which fit into complementary holes 66 in the washer 62. The cup 61 is capable of engaging and disengaging the washer 62 depending upon its direction of travel, while the washer 62 comprises protrusions 67 which allow it to move along and follow the thread pitch of the threads 55t of the lead screw portion 55 of the driver rod 53. In the embodiment of the invention shown in FIG. 23A, the lead screw portion 55 may comprise grooves 66g complementary to protrusions 67 in the washer 62. In the embodiment of the invention shown in FIGS. 24A and 24B, the engaging pins 65 of the washer 62 further comprises tangs 65t, and the cup 61 comprises ribs 71, which constrain the motion of the washer 62 further when the tangs 65t of the washer 62 contact the walls of the ribs 71.

Upon squeezing the lever 4, the translating member 64 is driven forward, moving the cup 61 forward at the same time (see dashed arrows in FIGS. 22A and B). When the motion of the cup 61 is initiated, the washer 62 is forced by the lead screw portion 55's threads 55t into contact with the cup 61. The engagement pins 65 of the cup 61 then engage with the washer 62. Once engaged, the washer 62 is no longer free to rotate or spin on the lead screw portion 55's threads 55t. As the translational member 64, cup 61, and washer 62, advance in a linear, forward direction, linear force from the force translating member 64 on the cup 61 is translated into rotary force upon the lead screw portion 55 of the driver rod 53, causing the driver rod 53 and the coupling member 59, which is coupled to it, to twist as the washer 62 follows the threads 55t of the lead screw portion 55. This twisting motion in turn applies a torque to a bone anchor screw 5 engaged by the coupling member 59, thereby screwing the bone anchor screw 5 into bone.

On the lever 4 return stroke, there is minimal linear force imposed upon the coupling member 59. The cup 61 provides the washer 62 with clearance to disengage from the engaging pins 65 of the cup 61 and to rotate freely as the washer 62 follows the threads 55t on the lead screw portion 55 of the driver rod 53. In a further embodiment of the invention, shown in FIG. 22B, a return coil spring 68 may provided at the barrel end 56 of the handle 2 to further apply a return compressive force on the cup 61 and translating member 64 when the lever 4 is released.

By incorporating a 60 degree pitch angle and 3-start thread, the complete seating of a bone anchor screw 5 can take place in approximately 10 strokes of the lever 4. The number of strokes can be reduced by optimizing thread 55t design, lever 4 stroke and/or cup 61/washer 62 clearance.

It should be readily apparent to one of ordinary skill in the art that the engaging pins 65 may be provided on the washer 62 side rather than the cup 61 side and that the holes 66 may be provided in the cup 61. The number of engagement pins 65 may also be varied. The engaging pins 65 may be an integral part of the washer 62 or cup 61, or may be removable from the washer 62 or cup 61. In addition, the number of starts in the multistart thread 55t of the lead screw portion 55 of the driver rod 53 may be varied from one through what ever number is dimensionally practical for the driver rod 53 diameter.

In a further embodiment of the invention as shown in FIGS. 22A, 22B, 24A, and 25B, a cover plate 63 is provided at the rim 69 of the cup 61 to contain the washer 62 within the cup 61 and to permit only minimal travel space for the washer 62 to move in when it is drawn free from the engaging pins 65 of the cup 61.

As with the previously disclosed manual bone anchor placement devices 1 and 36, the cup and washer manual bone anchor placement device 52 may be used with a bone anchor screw 5 with a pre-attached suture 7 which may be enclosed within a sleeve 24 press-fitted into a groove 23 cut into handle portion 2. The mating portion 59m of the coupling member may be configured to mate with a variety of bone anchor screws 5, and may comprise a shaft configured in a shape complementary to a recess in a bone anchor screw 5 or may comprise a recess complementary to a shaft in a bone anchor screw 5. As in the previously disclosed devices 1 and 36, the cup and washer manual bone anchor placement device 52 may include a modular design allowing for the interchange of different types of coupling members 59. The handle portion 2 may also be configured to include two separable halves which are able to snap-fit together, allowing removal of one driver rod and/or cup and washer assembly and replacement with another.

Self-Tapping Bone Anchor Screw

Figure 26:
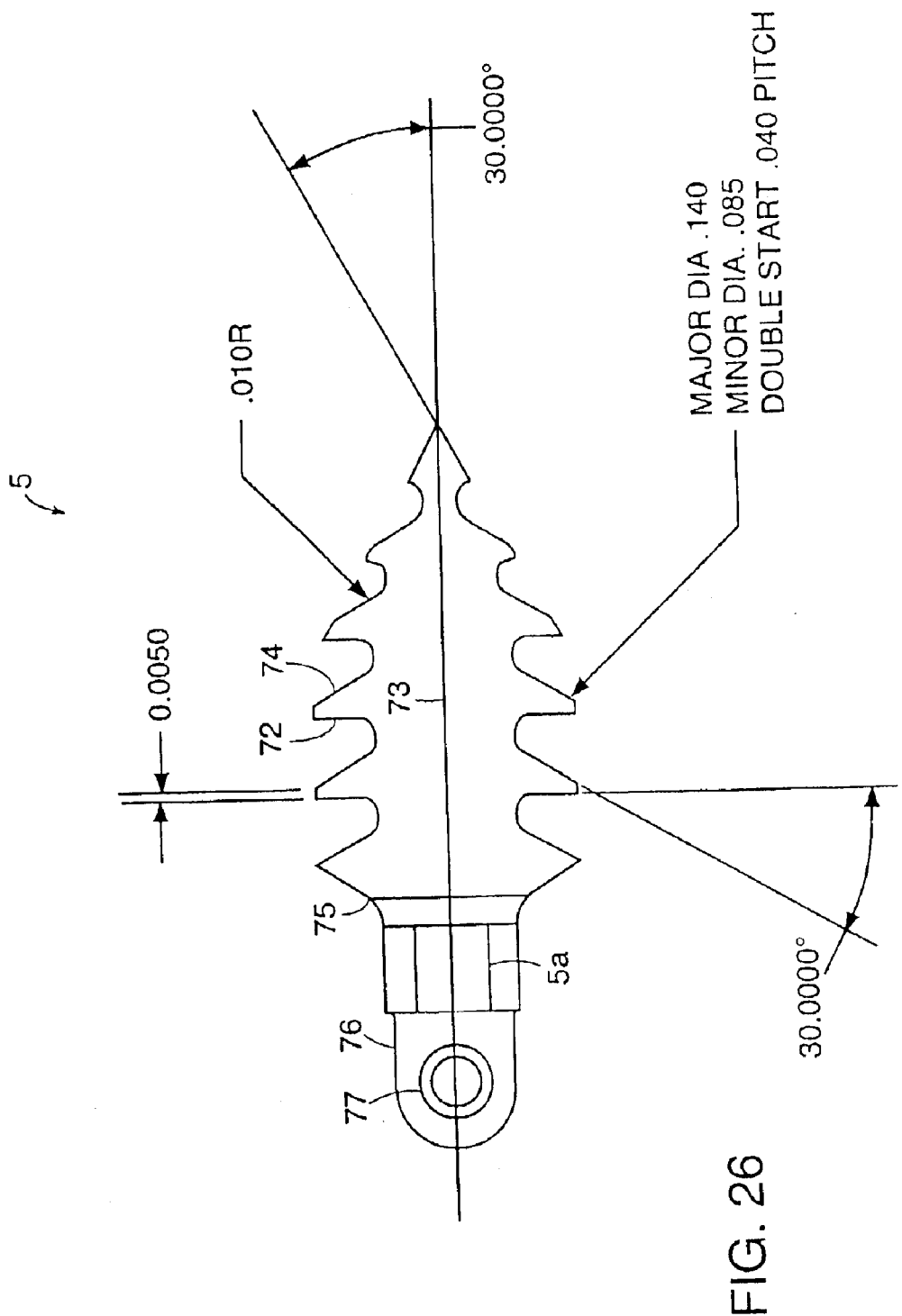
FIG. 26 shows a cross-section through a longitudinal axis of a self-tapping bone anchor screw according to one embodiment of the invention.

FIG. 26 shows a bone anchor screw 5 according to one embodiment of the invention. As shown in the FIG. 26, the threads of the bone anchor screw 5 are of buttress form. The forward face 72 of the screw thread is perpendicular to the longitudinal axis 73 of the bone anchor screw 5 while the back face 74 of the screw thread is at an acute angle relative to the longitudinal axis 73 of the bone anchor screw 5. The threads extend to the tip of the screw shank 75, reducing the amount of torque required to seat the bone anchor screw 5. In one embodiment of the invention, the back face 74 of the screw thread is at a 30 degree angle relative to forward face 72 of the screw thread.

The base 76 of the bone anchor screw 5 shown in FIG. 26A has an eyelet 77 which is circular and has micropolished edges. In another embodiment of the invention, the eyelet 77 at base 76 may be tear-drop shaped, or ellipsoidal. Other configurations may be used so long as the edges are rounded so as not to damage the suture 7. Micropolishing the eyelet 77 rounds the edges and reduces load to the suture 7 that may be caused by twisting (torsional load) during insertion, the user tugging on the suture 7 to test seating of the screw, and bodily movement while the anchor screw and suture are in place.

According to a further embodiment of the invention, kits including the disclosed self-tapping bone anchor screw may be provided for the convenience of the user. In one embodiment of the invention, a kit is provided, comprising at least one of: 1) a flexible, molded sleeve 24 for enclosing a suture 7, 2) a retaining clip 27 for preventing the suture 7 from slipping out of the sleeve 24, 3) a buttress-shaped bone anchor screw 5 comprising a micropolished eyelet 77 for receiving the suture 7, and 4) suture 7 material, which may or may not, be pre-attached to the bone anchor screw 5. The kit may comprise any one of these elements or combinations thereof.

Having thus described certain embodiments of the present invention, various alterations, modifications, and improvements will be obvious to those skilled in the art. Such variations, modifications and improvements are intended to be within the spirit and scope of the invention. The materials employed, as well as their shapes and dimensions, generally can vary. Accordingly, the foregoing description is by way of example only and is not intended to be limiting.

What is claimed is:

1. A manual bone anchor placement device, comprising:
   a manually-actuatable lever;
   a driver rod comprising threads;
   a cup coupled to the lever, positioned over the threads of the driver rod, and movable axially along the driver rod upon manual actuation of the lever; and
   a washer positioned over the threads of the driver rod, engaging the cup upon manual actuation of the lever, translating force from the lever to the driver rod, and rotating the driver rod.

2. The manual bone anchor placement device of claim 1, further comprising a coupling element for mating with a bone anchor screw, and for rotating when the driver rod rotates to place the bone anchor screw into bone.

3. The manual bone anchor placement device of claim 1, further comprising a force translating member coupled to the lever at a pivot and coupled to the cup by flanges on the cup, for translating force from the lever to the cup.

4. The manual bone anchor placement device of claim 1, further comprising a handle including a groove for receiving a suture attached to a bone anchor screw.

5. The manual bone anchor placement device of claim 1, wherein the washer further comprises at least one engaging pin for engaging the cup and the cup comprises holes for receiving the at least one engaging pin.

6. The manual bone anchor placement device of claim 1, wherein the cup further comprises at least one engaging pin for engaging the washer and the washer comprises holes for receiving the at least one engaging pin.

* * * * *